(12) United States Patent
Chin

(10) Patent No.: US 8,986,335 B2
(45) Date of Patent: Mar. 24, 2015

(54) TISSUE DISSECTOR APPARATUS AND METHOD

(71) Applicant: MAQUET Cardiovascular LLC, Mahwah, NJ (US)

(72) Inventor: Albert K Chin, Palo Alto, CA (US)

(73) Assignee: MAQUET Cardiovascular LLC, Mahwah, NJ (US)

( * ) Notice: Subject to any disclaimer, the term of this patent is extended or adjusted under 35 U.S.C. 154(b) by 0 days.

(21) Appl. No.: 13/914,546

(22) Filed: Jun. 10, 2013

(65) Prior Publication Data
US 2013/0274786 A1    Oct. 17, 2013

Related U.S. Application Data

(63) Continuation of application No. 13/092,826, filed on Apr. 22, 2011, now Pat. No. 8,460,331, which is a continuation of application No. 09/413,012, filed on Oct. 5, 1999, now Pat. No. 7,938,842, which is a continuation of application No. 09/133,136, filed on Aug. 12, 1998.

(51) Int. Cl.
*A61B 17/00* (2006.01)
*A61M 29/02* (2006.01)
*A61B 17/32* (2006.01)

(52) U.S. Cl.
CPC .......... *A61M 29/02* (2013.01); *A61B 17/00008* (2013.01); *A61B 17/320016* (2013.01); *A61B 17/32* (2013.01); *A61B 2017/320048* (2013.01)
USPC .......................................... 606/190; 600/127

(58) Field of Classification Search
USPC ........... 600/114, 127, 129; 606/190, 192, 198
See application file for complete search history.

(56) References Cited

U.S. PATENT DOCUMENTS

| 1,083,386 A | 1/1914 | Chapman |
| 1,422,826 A | 7/1922 | Brown |

(Continued)

FOREIGN PATENT DOCUMENTS

| AU | 199942354 A1 | 7/1999 |
| AU | 199935034 A1 | 1/2000 |

(Continued)

OTHER PUBLICATIONS

Historical Development of VasoView by Albert Chin.
(Continued)

*Primary Examiner* — Victor Nguyen

(57) ABSTRACT

Surgical apparatus and method includes a cannula that houses an endoscope and supports a dilating element near a distal end of the cannula. The dilating element has a dimension which is greater than the diameter of the cannula for enlarging a surgical cavity in tissue as the cannula is advanced through tissue at a surgical site to provide working space adjacent a target vessel within which surgical instruments may be conveniently manipulated. The dilating element of oval sided shape permits surrounding tissue to be pushed away or otherwise displaced away from the target vessel atraumatically. A locking mechanism is disposed on the cannula, which accepts a succession of mating dilating elements of progressively larger dimensions for successive insertion and enlargement of a surgical cavity as required. In one embodiment, the dilating element is made of rigid plastic, and in another embodiment, the dilating element is made of resilient material that may be confined within a retractable sheath which, in the extended position, encases and compresses the dilating element to a smaller dimension and which, in a retracted position, allows the dilating element to resiliently expand and enlarge the surgical cavity.

19 Claims, 10 Drawing Sheets

(56) References Cited

U.S. PATENT DOCUMENTS

| | | | |
|---|---|---|---|
| 1,683,708 | A | 9/1928 | Wappler et al. |
| 1,727,495 | A | 12/1928 | Wappler |
| 1,731,069 | A | 12/1928 | Herman |
| 1,741,461 | A | 12/1929 | Herman |
| 1,798,902 | A | 3/1931 | Raney |
| 1,867,624 | A | 7/1932 | Hoffman |
| 1,881,250 | A | 10/1932 | Tomlinson |
| 1,978,495 | A | 10/1934 | Landau |
| 2,001,169 | A | 5/1935 | Wallace |
| 2,002,594 | A | 5/1935 | Wappler et al. |
| 2,004,559 | A | 6/1935 | Wappler et al. |
| 2,011,169 | A | 8/1935 | Wappler |
| 2,012,937 | A | 9/1935 | Beuoy |
| 2,028,635 | A | 1/1936 | Wappler |
| 2,031,682 | A | 2/1936 | Wappler et al. |
| 2,162,681 | A | 6/1939 | Oval |
| 2,220,720 | A | 11/1940 | Jett |
| 2,227,727 | A | 1/1941 | Leggiadro |
| 2,316,297 | A | 4/1943 | Southerland et al. |
| 2,821,190 | A | 1/1958 | Chase |
| 2,840,070 | A | 6/1958 | Tofflemire |
| 2,868,206 | A | 1/1959 | Stoesser |
| 2,944,552 | A | 7/1960 | Cannon |
| 3,168,096 | A | 2/1965 | Brummelkamp |
| 3,185,155 | A | 5/1965 | Slaten et al. |
| 3,200,028 | A | 8/1965 | Chisholm |
| 3,224,320 | A | 12/1965 | Stenberg |
| 3,297,022 | A | 1/1967 | Wallace |
| 3,313,294 | A | 4/1967 | Olof |
| 3,336,916 | A | 8/1967 | Edlich |
| 3,354,478 | A | 11/1967 | Allen |
| 3,357,433 | A | 12/1967 | Fourestier et al. |
| 3,391,690 | A | 7/1968 | Thomas |
| 3,439,523 | A | 4/1969 | Wood |
| 3,568,677 | A | 3/1971 | Nolan et al. |
| 3,613,682 | A | 10/1971 | Naylor |
| 3,625,202 | A | 12/1971 | Oyoshirhara |
| 3,772,127 | A | 11/1973 | James |
| 3,805,793 | A | 4/1974 | Wright |
| 3,835,841 | A | 9/1974 | Terada |
| 3,856,016 | A | 12/1974 | Davis |
| 3,857,386 | A | 12/1974 | Ashbell |
| 3,866,601 | A | 2/1975 | Russell |
| 3,882,852 | A * | 5/1975 | Sinnreich ............... 600/104 |
| 3,882,854 | A | 5/1975 | Hulka et al. |
| 3,929,137 | A | 12/1975 | Gonser |
| 3,934,115 | A | 1/1976 | Peterson |
| 3,938,527 | A | 2/1976 | Rioux et al. |
| 3,980,861 | A | 9/1976 | Fukunaga |
| RE29,088 | E | 12/1976 | Shaw |
| 4,011,872 | A | 3/1977 | Komiya |
| 4,030,743 | A | 6/1977 | Warthen |
| 4,031,898 | A | 6/1977 | Hiltebrandt et al. |
| 4,038,987 | A | 8/1977 | Komiya |
| 4,052,980 | A | 10/1977 | Grams et al. |
| 4,132,227 | A | 1/1979 | Ibe |
| 4,175,545 | A | 11/1979 | Termanini |
| 4,178,920 | A | 12/1979 | Cawood et al. |
| 4,190,042 | A | 2/1980 | Sinnreich |
| 4,196,734 | A | 4/1980 | Harris |
| 4,213,460 | A | 7/1980 | Weiner |
| 4,232,660 | A | 11/1980 | Coles |
| 4,257,420 | A | 3/1981 | Terayama |
| 4,285,753 | A | 8/1981 | Warthen |
| 4,315,510 | A | 2/1982 | Kihn |
| 4,359,052 | A | 11/1982 | Staub |
| 4,362,160 | A | 12/1982 | Hiltebrandt |
| 4,369,768 | A | 1/1983 | Vukovic |
| 4,370,980 | A | 2/1983 | Lottick |
| 4,372,295 | A | 2/1983 | Heckele |
| 4,418,692 | A | 12/1983 | Guay |
| 4,423,727 | A | 1/1984 | Widran et al. |
| 4,428,746 | A | 1/1984 | Mendez |
| 4,440,170 | A | 4/1984 | Golden et al. |
| 4,493,320 | A | 1/1985 | Treat |
| 4,493,321 | A | 1/1985 | Leather |
| 4,493,711 | A | 1/1985 | Chin et al. |
| 4,499,898 | A | 2/1985 | Knepshield et al. |
| 4,499,899 | A | 2/1985 | Lyons, III |
| 4,516,574 | A | 5/1985 | Hewes, Jr. |
| 4,516,575 | A | 5/1985 | Gerhard et al. |
| 4,556,058 | A | 12/1985 | Green |
| 4,557,255 | A | 12/1985 | Goodman |
| 4,562,832 | A | 1/1986 | Wilder et al. |
| 4,586,919 | A | 5/1986 | Taheri |
| 4,587,968 | A | 5/1986 | Price |
| 4,597,030 | A | 6/1986 | Brody et al. |
| 4,597,379 | A | 7/1986 | Kihn et al. |
| 4,597,389 | A | 7/1986 | Ibrahim et al. |
| 4,600,940 | A | 7/1986 | Sluyter |
| 4,607,622 | A | 8/1986 | Fritch et al. |
| 4,638,802 | A | 1/1987 | Okada |
| 4,646,738 | A | 3/1987 | Trott |
| 4,649,917 | A | 3/1987 | Karasawa |
| 4,651,733 | A | 3/1987 | Mobin Uddin |
| 4,653,476 | A | 3/1987 | Bonnet |
| 4,654,024 | A | 3/1987 | Crittenden et al. |
| 4,655,216 | A | 4/1987 | Tischer |
| 4,656,999 | A | 4/1987 | Storz |
| 4,657,018 | A | 4/1987 | Hakky |
| 4,662,068 | A | 5/1987 | Polonsky |
| 4,667,655 | A | 5/1987 | Ogiu et al. |
| 4,671,274 | A | 6/1987 | Sorochenko |
| 4,700,694 | A | 10/1987 | Shishido |
| 4,702,246 | A | 10/1987 | Ellis et al. |
| 4,705,041 | A | 11/1987 | Kim, II |
| 4,726,370 | A | 2/1988 | Karasawa et al. |
| 4,744,363 | A | 5/1988 | Hasson |
| 4,745,908 | A | 5/1988 | Wardle |
| 4,754,754 | A | 7/1988 | Garito et al. |
| 4,759,348 | A | 7/1988 | Cawood |
| 4,759,364 | A | 7/1988 | Boebel |
| 4,762,120 | A | 8/1988 | Hussein |
| 4,768,508 | A | 9/1988 | Chin et al. |
| 4,772,093 | A | 9/1988 | Abele et al. |
| 4,773,394 | A | 9/1988 | Reichstein et al. |
| 4,779,611 | A | 10/1988 | Grooters et al. |
| 4,793,346 | A | 12/1988 | Mindich |
| 4,819,620 | A | 4/1989 | Okutsu |
| 4,819,633 | A | 4/1989 | Bauer et al. |
| 4,821,718 | A | 4/1989 | Uldall |
| 4,838,246 | A | 6/1989 | Hahn et al. |
| 4,858,595 | A | 8/1989 | Buess et al. |
| 4,862,874 | A | 9/1989 | Kellner |
| 4,865,019 | A | 9/1989 | Phillips |
| 4,867,138 | A | 9/1989 | Kubota et al. |
| 4,869,268 | A | 9/1989 | Yoon |
| 4,874,375 | A | 10/1989 | Ellison |
| 4,877,016 | A | 10/1989 | Kantor et al. |
| 4,919,129 | A | 4/1990 | Weber et al. |
| 4,924,851 | A | 5/1990 | Ognier et al. |
| 4,924,882 | A | 5/1990 | Donovan |
| 4,931,042 | A | 6/1990 | Holmes et al. |
| 4,932,952 | A | 6/1990 | Wojciechowicz, Jr. |
| 4,936,842 | A | 6/1990 | D'Amelio et al. |
| 4,950,278 | A | 8/1990 | Sachse et al. |
| 4,959,067 | A | 9/1990 | Muller |
| 4,966,596 | A | 10/1990 | Kuntz et al. |
| 4,979,771 | A | 12/1990 | Childs, III |
| 4,985,030 | A | 1/1991 | Melzer et al. |
| 4,991,565 | A | 2/1991 | Takahashi et al. |
| 4,994,062 | A | 2/1991 | Nishigaki et al. |
| 4,997,419 | A | 3/1991 | Lakatos et al. |
| 4,997,436 | A | 3/1991 | Oberlander |
| 4,998,527 | A | 3/1991 | Meyer |
| 4,998,972 | A | 3/1991 | Chin et al. |
| 5,007,898 | A | 4/1991 | Rosenbluth et al. |
| 5,007,907 | A | 4/1991 | Nishigaki et al. |
| 5,007,908 | A | 4/1991 | Rydell |
| 5,011,490 | A | 4/1991 | Fischell et al. |
| 5,013,312 | A | 5/1991 | Parins et al. |
| 5,020,514 | A | 6/1991 | Heckele |
| 5,025,778 | A | 6/1991 | Silverstein et al. |
| 5,026,370 | A | 6/1991 | Lottick |

(56) References Cited

U.S. PATENT DOCUMENTS

| | | |
|---|---|---|
| 5,026,383 A | 6/1991 | Nobles |
| 5,035,232 A | 7/1991 | Lutze et al. |
| 5,037,433 A | 8/1991 | Wilk et al. |
| 5,046,251 A | 9/1991 | Scott |
| 5,047,038 A | 9/1991 | Peters et al. |
| 5,049,154 A | 9/1991 | Quadri |
| 5,053,041 A | 10/1991 | Ansari et al. |
| 5,100,420 A | 3/1992 | Green et al. |
| 5,122,137 A | 6/1992 | Lennox |
| 5,139,508 A | 8/1992 | Kantrowitz et al. |
| 5,147,356 A | 9/1992 | Bhatta |
| 5,151,102 A | 9/1992 | Kamiyama et al. |
| 5,171,255 A | 12/1992 | Rydell |
| 5,171,311 A | 12/1992 | Rydell et al. |
| 5,181,919 A | 1/1993 | Bergman et al. |
| 5,188,630 A | 2/1993 | Christoudias |
| 5,190,541 A | 3/1993 | Abele et al. |
| 5,192,280 A | 3/1993 | Parins |
| 5,197,649 A | 3/1993 | Bessler et al. |
| 5,197,971 A | 3/1993 | Bonutti |
| 5,201,752 A | 4/1993 | Brown et al. |
| 5,203,773 A | 4/1993 | Green |
| 5,207,691 A | 5/1993 | Nardella |
| 5,213,093 A | 5/1993 | Swindle |
| 5,217,001 A | 6/1993 | Nakao et al. |
| 5,217,441 A | 6/1993 | Shichman |
| 5,217,458 A | 6/1993 | Parins |
| 5,226,890 A * | 7/1993 | Ianniruberto et al. ... 604/164.04 |
| 5,226,908 A | 7/1993 | Yoon |
| 5,230,621 A | 7/1993 | Jacoby |
| 5,250,046 A | 10/1993 | Lee |
| 5,251,613 A | 10/1993 | Adair |
| 5,258,006 A | 11/1993 | Rydell et al. |
| 5,259,366 A | 11/1993 | Reydel et al. |
| 5,267,998 A | 12/1993 | Hagen |
| 5,269,753 A | 12/1993 | Wilk |
| 5,269,785 A | 12/1993 | Bonutti |
| 5,271,380 A | 12/1993 | Riek et al. |
| 5,271,385 A | 12/1993 | Bailey |
| 5,273,026 A | 12/1993 | Wilk |
| 5,275,608 A | 1/1994 | Forman et al. |
| 5,276,306 A | 1/1994 | Huffman |
| 5,279,546 A | 1/1994 | Mische et al. |
| 5,279,565 A | 1/1994 | Klein et al. |
| 5,284,128 A | 2/1994 | Hart |
| 5,284,478 A | 2/1994 | Nobles et al. |
| 5,290,249 A | 3/1994 | Foster et al. |
| 5,290,284 A | 3/1994 | Adair |
| 5,290,286 A | 3/1994 | Parins |
| 5,295,994 A | 3/1994 | Bonutti |
| 5,300,036 A | 4/1994 | Mueller et al. |
| 5,312,423 A | 5/1994 | Rosenbluth et al. |
| 5,318,564 A | 6/1994 | Eggers |
| 5,318,586 A | 6/1994 | Ereren |
| 5,320,115 A | 6/1994 | Kenna |
| 5,322,503 A | 6/1994 | Desai |
| 5,330,497 A | 7/1994 | Freitas et al. |
| 5,334,150 A | 8/1994 | Kaali |
| 5,336,221 A | 8/1994 | Anderson |
| 5,336,229 A | 8/1994 | Noda |
| 5,336,231 A | 8/1994 | Adair |
| 5,337,736 A | 8/1994 | Reddy |
| 5,339,803 A | 8/1994 | Mayzels et al. |
| 5,345,927 A | 9/1994 | Bonutti |
| 5,346,504 A | 9/1994 | Ortiz et al. |
| 5,352,219 A | 10/1994 | Reddy |
| 5,352,222 A | 10/1994 | Rydell |
| 5,354,291 A | 10/1994 | Bales et al. |
| 5,359,995 A | 11/1994 | Sewell, Jr. |
| 5,360,428 A | 11/1994 | Hutchinson, Jr. |
| 5,366,476 A | 11/1994 | Noda |
| 5,368,015 A | 11/1994 | Wilk |
| 5,370,109 A | 12/1994 | Cuny |
| 5,373,840 A | 12/1994 | Knighton |
| 5,374,277 A | 12/1994 | Hassler |
| 5,376,076 A | 12/1994 | Kaali |
| 5,376,087 A | 12/1994 | Haber et al. |
| 5,380,291 A | 1/1995 | Kaali |
| 5,383,889 A | 1/1995 | Warner et al. |
| 5,385,572 A | 1/1995 | Nobles et al. |
| 5,386,818 A | 2/1995 | Schneebaum et al. |
| 5,389,098 A | 2/1995 | Tsuruta et al. |
| 5,391,178 A | 2/1995 | Yapor |
| 5,395,367 A | 3/1995 | Wilk |
| 5,395,383 A | 3/1995 | Adams et al. |
| 5,397,335 A | 3/1995 | Gresl et al. |
| 5,401,273 A | 3/1995 | Shippert |
| 5,403,312 A | 4/1995 | Yates et al. |
| 5,411,466 A | 5/1995 | Hess |
| 5,411,483 A | 5/1995 | Loomas et al. |
| 5,411,508 A | 5/1995 | Bessler et al. |
| 5,417,697 A | 5/1995 | Wilk et al. |
| 5,419,309 A | 5/1995 | Biehl |
| 5,423,813 A | 6/1995 | Kaiser et al. |
| 5,424,877 A | 6/1995 | Tsuyuki et al. |
| 5,425,355 A | 6/1995 | Kulick |
| 5,425,357 A | 6/1995 | Moll et al. |
| 5,431,151 A | 7/1995 | Riek et al. |
| 5,441,041 A | 8/1995 | Sauer et al. |
| 5,441,044 A | 8/1995 | Tovey et al. |
| 5,441,498 A | 8/1995 | Perkins |
| 5,443,463 A | 8/1995 | Stern et al. |
| 5,445,638 A | 8/1995 | Rydell |
| 5,447,502 A | 9/1995 | Haaga |
| 5,447,513 A | 9/1995 | Davison et al. |
| 5,448,990 A | 9/1995 | De Faria Correa |
| 5,450,842 A | 9/1995 | Tovey et al. |
| 5,451,223 A | 9/1995 | Ben-Simhon |
| 5,452,513 A | 9/1995 | Zinnbauer et al. |
| 5,452,732 A | 9/1995 | Bircoll |
| 5,454,365 A | 10/1995 | Bonutti |
| 5,458,598 A | 10/1995 | Feinberg et al. |
| 5,460,629 A | 10/1995 | Shlain et al. |
| 5,468,248 A | 11/1995 | Chin et al. |
| 5,474,057 A | 12/1995 | Makower et al. |
| 5,480,409 A | 1/1996 | Riza |
| 5,486,155 A | 1/1996 | Muller et al. |
| 5,489,290 A | 2/1996 | Furnish |
| 5,490,836 A | 2/1996 | Desai |
| 5,496,317 A | 3/1996 | Goble et al. |
| 5,496,345 A | 3/1996 | Kieturakis et al. |
| 5,501,654 A | 3/1996 | Failla et al. |
| 5,505,686 A | 4/1996 | Willis et al. |
| 5,507,755 A | 4/1996 | Gresl et al. |
| 5,509,922 A | 4/1996 | Aranyi et al. |
| 5,511,564 A | 4/1996 | Wilk |
| 5,512,037 A | 4/1996 | Russell et al. |
| 5,512,721 A | 4/1996 | Young et al. |
| 5,514,151 A | 5/1996 | Fogarty et al. |
| 5,514,153 A | 5/1996 | Bonutti |
| 5,514,236 A | 5/1996 | Avellanet et al. |
| 5,522,830 A | 6/1996 | Aranyi |
| 5,527,331 A | 6/1996 | Kresch et al. |
| 5,533,496 A | 7/1996 | De Faria Correa et al. |
| 5,535,759 A | 7/1996 | Wilk |
| 5,536,251 A | 7/1996 | Evard et al. |
| 5,540,711 A | 7/1996 | Kieturakis et al. |
| 5,549,605 A | 8/1996 | Hahnen |
| 5,549,636 A | 8/1996 | Li |
| 5,549,637 A | 8/1996 | Crainich |
| 5,551,947 A | 9/1996 | Kaali |
| 5,554,101 A | 9/1996 | Matula et al. |
| 5,556,563 A | 9/1996 | von der Heyde et al. |
| 5,558,620 A | 9/1996 | Heckele et al. |
| 5,564,615 A | 10/1996 | Bishop et al. |
| 5,565,122 A | 10/1996 | Zinnbauer et al. |
| 5,569,164 A | 10/1996 | Lurz |
| 5,569,183 A | 10/1996 | Kieturakis |
| 5,569,244 A | 10/1996 | Hahnen |
| 5,569,274 A | 10/1996 | Rapacki et al. |
| 5,569,291 A | 10/1996 | Privitera et al. |
| 5,571,100 A | 11/1996 | Goble |
| 5,575,756 A | 11/1996 | Karasawa et al. |
| 5,582,611 A | 12/1996 | Tsuruta et al. |

(56) References Cited

U.S. PATENT DOCUMENTS

| | | | |
|---|---|---|---|
| 5,588,581 A | 12/1996 | Conlon et al. |
| 5,591,183 A | 1/1997 | Chin |
| 5,593,418 A | 1/1997 | Mollenauer |
| 5,595,565 A | 1/1997 | Treat et al. |
| 5,599,349 A | 2/1997 | D'Amelio |
| 5,601,580 A | 2/1997 | Goldberg et al. |
| 5,601,581 A | 2/1997 | Fogarty et al. |
| 5,601,589 A | 2/1997 | Fogarty et al. |
| 5,601,601 A | 2/1997 | Tal et al. |
| 5,603,698 A | 2/1997 | Roberts et al. |
| 5,607,441 A | 3/1997 | Sierocuk et al. |
| 5,607,443 A | 3/1997 | Kieturakis et al. |
| 5,618,307 A | 4/1997 | Donlon et al. |
| 5,626,587 A | 5/1997 | Bishop et al. |
| 5,630,787 A | 5/1997 | Yabe et al. |
| 5,630,795 A | 5/1997 | Kuramoto et al. |
| 5,634,584 A | 6/1997 | Okorocha et al. |
| 5,634,924 A | 6/1997 | Turkel et al. |
| 5,647,871 A | 7/1997 | Levine et al. |
| 5,653,722 A | 8/1997 | Kieturakis |
| 5,653,726 A | 8/1997 | Kieturakis |
| 5,656,012 A | 8/1997 | Sienkiewicz |
| 5,658,282 A | 8/1997 | Daw et al. |
| 5,662,585 A | 9/1997 | Willis et al. |
| 5,662,588 A | 9/1997 | Iida |
| 5,662,662 A | 9/1997 | Bishop et al. |
| 5,665,085 A | 9/1997 | Nardella |
| 5,665,096 A | 9/1997 | Yoon |
| 5,667,480 A | 9/1997 | Knight et al. |
| 5,667,520 A | 9/1997 | Bonutti |
| 5,669,906 A | 9/1997 | Grossi et al. |
| 5,673,840 A | 10/1997 | Schulze et al. |
| 5,680,982 A | 10/1997 | Schulze et al. |
| 5,683,349 A | 11/1997 | Makower et al. |
| 5,685,820 A | 11/1997 | Riek et al. |
| 5,685,826 A | 11/1997 | Bonutti |
| 5,688,269 A | 11/1997 | Newton et al. |
| 5,688,270 A | 11/1997 | Yates et al. |
| 5,688,286 A | 11/1997 | Yoon |
| 5,690,606 A | 11/1997 | Slotman |
| 5,690,847 A | 11/1997 | LaValley et al. |
| 5,693,051 A | 12/1997 | Schulze et al. |
| 5,695,448 A | 12/1997 | Kimura et al. |
| 5,700,236 A | 12/1997 | Sauer et al. |
| 5,702,408 A | 12/1997 | Wales et al. |
| 5,702,412 A | 12/1997 | Popov et al. |
| 5,702,417 A | 12/1997 | Hermann |
| 5,704,372 A | 1/1998 | Moll et al. |
| 5,704,534 A | 1/1998 | Huitema et al. |
| 5,707,382 A | 1/1998 | Sierocuk et al. |
| 5,707,389 A | 1/1998 | Louw et al. |
| 5,707,390 A | 1/1998 | Bonutti |
| 5,709,680 A | 1/1998 | Yates et al. |
| 5,713,505 A | 2/1998 | Huitema |
| 5,716,325 A | 2/1998 | Bonutti |
| 5,716,352 A | 2/1998 | Viola et al. |
| 5,718,714 A | 2/1998 | Livneh |
| 5,720,761 A | 2/1998 | Kaali |
| 5,720,763 A | 2/1998 | Tovey |
| 5,722,934 A | 3/1998 | Knight et al. |
| 5,725,479 A | 3/1998 | Knight et al. |
| 5,728,119 A | 3/1998 | Smith et al. |
| 5,730,748 A | 3/1998 | Fogarty et al. |
| 5,730,756 A | 3/1998 | Kieturakis et al. |
| 5,735,848 A | 4/1998 | Yates et al. |
| 5,738,628 A | 4/1998 | Sierocuk et al. |
| 5,743,880 A | 4/1998 | Hlavka |
| 5,749,870 A | 5/1998 | Gloth et al. |
| 5,752,966 A | 5/1998 | Chang |
| 5,755,717 A | 5/1998 | Yates et al. |
| 5,759,150 A | 6/1998 | Konou et al. |
| 5,759,183 A | 6/1998 | VanDusseldorp |
| 5,759,188 A | 6/1998 | Yoon |
| 5,762,606 A | 6/1998 | Minnich |
| 5,766,169 A | 6/1998 | Fritzsch et al. |
| 5,766,215 A | 6/1998 | Muri et al. |
| 5,772,576 A | 6/1998 | Knighton et al. |
| 5,776,112 A | 7/1998 | Stephens et al. |
| 5,779,728 A | 7/1998 | Lunsford et al. |
| 5,795,331 A | 8/1998 | Cragg et al. |
| 5,797,907 A | 8/1998 | Clement |
| 5,807,393 A | 9/1998 | Williamson et al. |
| 5,810,811 A | 9/1998 | Yates et al. |
| 5,817,013 A | 10/1998 | Ginn et al. |
| 5,817,061 A * | 10/1998 | Goodwin et al. ........ 604/164.03 |
| 5,817,062 A | 10/1998 | Flom et al. |
| 5,827,279 A | 10/1998 | Hughett et al. |
| 5,827,281 A | 10/1998 | Levin |
| 5,827,318 A | 10/1998 | Bonutti |
| 5,843,017 A | 12/1998 | Yoon |
| 5,843,121 A | 12/1998 | Yoon |
| RE36,043 E | 1/1999 | Knighton |
| 5,857,961 A | 1/1999 | Vanden Hoek et al. |
| 5,860,997 A | 1/1999 | Bonutti |
| 5,868,785 A | 2/1999 | Tal et al. |
| 5,871,496 A | 2/1999 | Ginn et al. |
| 5,871,498 A | 2/1999 | Jervis et al. |
| 5,873,889 A | 2/1999 | Chin |
| 5,895,352 A | 4/1999 | Kleiner |
| 5,895,353 A | 4/1999 | Lunsford et al. |
| 5,897,487 A | 4/1999 | Ouchi |
| 5,908,429 A | 6/1999 | Yoon |
| 5,913,870 A | 6/1999 | DeFonzo et al. |
| 5,914,062 A | 6/1999 | von der Heyde |
| 5,916,213 A | 6/1999 | Haissaguerre et al. |
| 5,921,993 A | 7/1999 | Yoon |
| 5,925,058 A | 7/1999 | Smith et al. |
| 5,928,135 A | 7/1999 | Knight et al. |
| 5,928,138 A | 7/1999 | Knight et al. |
| 5,938,620 A | 8/1999 | Daxer |
| 5,944,732 A | 8/1999 | Raulerson et al. |
| 5,957,923 A | 9/1999 | Hahnen et al. |
| 5,957,936 A | 9/1999 | Yoon et al. |
| 5,976,130 A | 11/1999 | McBrayer et al. |
| 5,980,549 A | 11/1999 | Chin |
| 5,984,937 A | 11/1999 | Morse et al. |
| 5,984,938 A | 11/1999 | Yoon |
| 5,984,939 A | 11/1999 | Yoon |
| 5,993,384 A | 11/1999 | Lunsford et al. |
| 6,015,423 A | 1/2000 | Andrese |
| 6,036,713 A | 3/2000 | Kieturakis |
| 6,059,802 A | 5/2000 | Ginn |
| 6,071,232 A | 6/2000 | Knighton et al. |
| 6,077,277 A | 6/2000 | Mollenauer et al. |
| 6,080,102 A | 6/2000 | Konou et al. |
| 6,120,434 A | 9/2000 | Kimura et al. |
| 6,123,689 A | 9/2000 | To et al. |
| H1904 H | 10/2000 | Yates et al. |
| 6,129,661 A | 10/2000 | Iafrati et al. |
| 6,162,173 A | 12/2000 | Chin et al. |
| 6,176,825 B1 | 1/2001 | Chin et al. |
| 6,186,825 B1 | 2/2001 | Bogiel et al. |
| 6,234,958 B1 | 5/2001 | Snoke et al. |
| 6,277,137 B1 | 8/2001 | Chin |
| 6,287,304 B1 | 9/2001 | Eggers et al. |
| 6,312,442 B1 | 11/2001 | Kieturakis et al. |
| 6,348,037 B1 | 2/2002 | Chin et al. |
| 6,361,543 B1 | 3/2002 | Chin et al. |
| 6,387,043 B1 | 5/2002 | Yoon |
| 6,406,425 B1 | 6/2002 | Chin et al. |
| 6,432,115 B1 | 8/2002 | Mollenauer et al. |
| 6,520,975 B2 | 2/2003 | Branco |
| 6,544,260 B1 | 4/2003 | Markel et al. |
| 6,558,313 B1 | 5/2003 | Knighton et al. |
| 6,562,051 B1 | 5/2003 | Bolduc et al. |
| 6,648,898 B1 | 11/2003 | Baxter |
| 6,660,016 B2 | 12/2003 | Lindsay |
| 6,673,087 B1 | 1/2004 | Chang et al. |
| 6,702,813 B1 | 3/2004 | Baxter et al. |
| 6,705,986 B2 | 3/2004 | Fiegel et al. |
| 6,730,020 B2 | 5/2004 | Peng et al. |
| 6,749,609 B1 | 6/2004 | Lunsford et al. |
| 6,752,756 B2 | 6/2004 | Lunsford et al. |
| 6,762,368 B2 | 7/2004 | Saputro et al. |

(56) References Cited

U.S. PATENT DOCUMENTS

| | | |
|---|---|---|
| 6,811,546 B1 | 11/2004 | Callas et al. |
| 6,814,696 B1 | 11/2004 | Chang et al. |
| 6,814,743 B2 | 11/2004 | Chin et al. |
| 6,830,546 B1 | 12/2004 | Chin et al. |
| 6,884,248 B2 | 4/2005 | Bolduc et al. |
| 6,899,670 B2 | 5/2005 | Peng et al. |
| 6,951,568 B1 | 10/2005 | Chin |
| 6,963,792 B1 | 11/2005 | Green |
| 6,972,028 B2 | 12/2005 | Chin |
| 6,976,957 B1 | 12/2005 | Chin et al. |
| 7,033,357 B2 | 4/2006 | Baxter et al. |
| 7,066,875 B2 | 6/2006 | Knighton et al. |
| 7,097,665 B2 | 8/2006 | Stack et al. |
| 7,146,984 B2 | 12/2006 | Stack et al. |
| 7,211,040 B2 | 5/2007 | Knighton et al. |
| 7,214,180 B2 | 5/2007 | Chin |
| 7,226,409 B2 | 6/2007 | Peng et al. |
| 7,264,587 B2 | 9/2007 | Chin |
| 7,288,096 B2 | 10/2007 | Chin |
| 7,326,178 B1 | 2/2008 | Lunsford et al. |
| 7,344,536 B1 | 3/2008 | Lunsford et al. |
| 7,364,657 B2 | 4/2008 | Mandrusov et al. |
| 7,384,423 B1 | 6/2008 | Chin |
| 7,398,781 B1 | 7/2008 | Chin |
| 7,431,725 B2 | 10/2008 | Stack et al. |
| 7,476,198 B1 | 1/2009 | Chin et al. |
| 7,479,104 B2 | 1/2009 | Lau et al. |
| 7,485,092 B1 | 2/2009 | Stewart et al. |
| 7,534,243 B1 | 5/2009 | Chin et al. |
| 7,695,470 B1 | 4/2010 | Stewart et al. |
| 7,938,842 B1 | 5/2011 | Chin |
| 8,075,559 B2 | 12/2011 | Stewart et al. |
| 2002/0128542 A1 | 9/2002 | Van Over |
| 2002/0183593 A1 | 12/2002 | Chin et al. |
| 2003/0187460 A1 | 10/2003 | Chin et al. |
| 2003/0187461 A1 | 10/2003 | Chin |
| 2003/0236544 A1 | 12/2003 | Lunsford et al. |
| 2004/0097792 A1 | 5/2004 | Moll et al. |
| 2004/0102804 A1 | 5/2004 | Chin |
| 2004/0153098 A1 | 8/2004 | Chin et al. |
| 2004/0153101 A1 | 8/2004 | Bolduc et al. |
| 2004/0181242 A1 | 9/2004 | Stack et al. |
| 2004/0216748 A1 | 11/2004 | Chin |
| 2004/0236231 A1 | 11/2004 | Knighton et al. |
| 2004/0236310 A1 | 11/2004 | Chin et al. |
| 2005/0020911 A1 | 1/2005 | Viswanathan |
| 2005/0192613 A1 | 9/2005 | Lindsay |
| 2005/0247320 A1 | 11/2005 | Stack et al. |
| 2005/0261712 A1 | 11/2005 | Balbierz et al. |
| 2005/0266109 A1 | 12/2005 | Chin et al. |
| 2005/0267499 A1 | 12/2005 | Stack et al. |
| 2005/0283380 A1 | 12/2005 | Garduno |
| 2006/0052660 A1 | 3/2006 | Chin |
| 2006/0074337 A1 | 4/2006 | Yoo |
| 2006/0079915 A1 | 4/2006 | Chin et al. |
| 2006/0116746 A1 | 6/2006 | Chin |
| 2006/0206121 A1 | 9/2006 | Chin et al. |
| 2006/0270900 A1 | 11/2006 | Chin et al. |
| 2006/0271032 A1 | 11/2006 | Chin et al. |
| 2006/0287574 A1 | 12/2006 | Chin |
| 2006/0287734 A1 | 12/2006 | Stack et al. |
| 2007/0060932 A1 | 3/2007 | Stack et al. |
| 2007/0118206 A1 | 5/2007 | Colgan et al. |
| 2007/0123799 A1 | 5/2007 | Meireles |
| 2007/0162067 A1 | 7/2007 | Lunsford et al. |
| 2007/0167692 A1 | 7/2007 | Kim |
| 2007/0198043 A1 | 8/2007 | Cox et al. |
| 2007/0219571 A1 | 9/2007 | Balbierz et al. |
| 2007/0238917 A1 | 10/2007 | Peng et al. |
| 2007/0276432 A1 | 11/2007 | Stack et al. |
| 2008/0039879 A1 | 2/2008 | Chin et al. |
| 2008/0065122 A1 | 3/2008 | Stack et al. |
| 2008/0097523 A1 | 4/2008 | Bolduc et al. |
| 2008/0103365 A1 | 5/2008 | Lunsford et al. |
| 2008/0132892 A1 | 6/2008 | Lunsford et al. |
| 2008/0145345 A1 | 6/2008 | Mandrusov et al. |
| 2008/0145469 A1 | 6/2008 | Chin et al. |
| 2008/0306333 A1 | 12/2008 | Chin |
| 2008/0306335 A1 | 12/2008 | Lau et al. |
| 2009/0023986 A1 | 1/2009 | Stewart |
| 2009/0024156 A1 | 1/2009 | Chin |
| 2009/0062610 A1 | 3/2009 | Williams |
| 2009/0112122 A1 | 4/2009 | Chuang |
| 2009/0281388 A1 | 11/2009 | Ito |
| 2009/0322513 A1 | 12/2009 | Hwang |
| 2009/0326372 A1 | 12/2009 | Darlington |
| 2010/0234843 A1 | 9/2010 | Stewart |
| 2011/0202082 A1 | 8/2011 | Chin |
| 2012/0078037 A1 | 3/2012 | Stewart |

FOREIGN PATENT DOCUMENTS

| | | |
|---|---|---|
| AU | 719712 B2 | 5/2000 |
| AU | 2007203086 A1 | 1/2009 |
| CA | 2244164 A1 | 7/1997 |
| CA | 2274270 A1 | 12/1999 |
| CA | 2279661 A1 | 2/2000 |
| CA | 2592766 A1 | 12/2008 |
| DE | 24669 C | 5/1883 |
| DE | 40469 C | 8/1887 |
| DE | H246691 C | 10/1956 |
| DE | 2415263 A1 | 10/1975 |
| DE | 2550693 A1 | 5/1977 |
| DE | 3002088 A1 | 7/1981 |
| DE | 3525917 A1 | 2/1986 |
| DE | 40469 C | 8/1987 |
| DE | 3942589 A1 | 7/1991 |
| EP | 131347 A2 | 1/1985 |
| EP | 131347 A3 | 3/1986 |
| EP | 0243714 A2 | 11/1987 |
| EP | 341943 A2 | 11/1989 |
| EP | 409569 A1 | 1/1991 |
| EP | 517244 A1 | 12/1992 |
| EP | 518230 A1 | 12/1992 |
| EP | 664104 A2 | 7/1995 |
| EP | 681811 A2 | 11/1995 |
| EP | 517244 B1 | 3/1996 |
| EP | 518230 B1 | 5/1996 |
| EP | 761171 A2 | 3/1997 |
| EP | 769270 A1 | 4/1997 |
| EP | 867148 A1 | 9/1998 |
| EP | 878168 A1 | 11/1998 |
| EP | 0878168 A1 | 11/1998 |
| EP | 0979635 A2 | 2/2000 |
| EP | 0980673 A2 | 2/2000 |
| EP | 761171 B1 | 3/2005 |
| FR | 2265344 A1 | 10/1975 |
| FR | 2265344 B3 | 12/1977 |
| GB | 2082459 A | 3/1982 |
| GB | 2195540 A | 4/1988 |
| JP | 7027043 A | 1/1995 |
| JP | 2802244 A | 7/1998 |
| JP | 11172954 A | 6/1999 |
| JP | 11225282 A | 8/1999 |
| JP | 2000037389 A | 2/2000 |
| JP | 2000051221 A2 | 2/2000 |
| JP | 2007509702 T | 4/2007 |
| JP | 2007175478 A | 7/2007 |
| SU | 510235 A1 | 4/1976 |
| SU | 639545 A1 | 12/1978 |
| SU | 1371689 A1 | 2/1988 |
| SU | 1498474 A1 | 8/1989 |
| WO | 9108710 A1 | 6/1991 |
| WO | 9208513 A1 | 5/1992 |
| WO | 9220291 A1 | 11/1992 |
| WO | 9308754 A1 | 5/1993 |
| WO | 9418881 A1 | 9/1994 |
| WO | 9424949 A1 | 11/1994 |
| WO | 9424951 A1 | 11/1994 |
| WO | 9510982 A1 | 4/1995 |
| WO | 9519737 A1 | 7/1995 |
| WO | 9601130 A1 | 1/1996 |
| WO | 9630072 A1 | 10/1996 |
| WO | 9716125 A1 | 5/1997 |

(56) References Cited

FOREIGN PATENT DOCUMENTS

| | | |
|---|---|---|
| WO | 9726831 A1 | 7/1997 |
| WO | 9733522 A1 | 9/1997 |
| WO | 9737701 A1 | 10/1997 |
| WO | 9802084 A2 | 1/1998 |
| WO | 9802102 A2 | 1/1998 |
| WO | 9806451 A1 | 2/1998 |
| WO | 9802102 A3 | 3/1998 |
| WO | 9838935 A1 | 9/1998 |
| WO | 0040139 A1 | 7/2000 |
| WO | 0040160 A2 | 7/2000 |
| WO | 03057062 A2 | 7/2003 |
| WO | 03094758 A1 | 11/2003 |
| WO | 03105706 A1 | 12/2003 |
| WO | 2004066828 A2 | 8/2004 |
| WO | 2004066829 A2 | 8/2004 |
| WO | 2004073506 A2 | 9/2004 |
| WO | 2005006955 A2 | 1/2005 |
| WO | 2005044079 A2 | 5/2005 |
| WO | 2009036287 A1 | 3/2009 |

OTHER PUBLICATIONS

Pending U.S. Appl. No. 10/897,157.
Initial Expert Report of Paul Mitiguy, Oct. 31, 2008.
Customer Needs Assessment.
VasoView Issue.
Memorandum re VasoView Feedback, Aug. 29, 1996.
Memorandum re VasoView Continued Release Plan, Dec. 11, 1996.
Handwritten Notes.
VasoView 2 Thoughts by Scott C. Anderson, Oct. 10, 1996.
Excerpt from Frazier Lab Notebook No. 144, Jun. 9, 1997.
Excerpt from Frazier Lab Notebook No. 152, Jun. 9, 1997.
Clinical Results.
Orbital Dissection Cannula Product Specification, Jun. 7, 1997.
Attachment A PPAQ Approval, Design Review, Design Freeze, Apr. 15, 1997.
VasoView Oribital Dissector Dissection Cannula lfu, Mar. 14, 1997.
Page from Tachi Callas Lab Notebook.
Senior Staff update, May 5, 1997.
Disengagement project Scope for Enhanced Orbital Dissector, Dec. 18, 1997.
Excerpt from Frazier Lab Notebook No. 144, Nov. 3, 1997.
Excerpt from Tachi Callas Lab notebook No. 152, Nov. 3, 1997.
Orbital Dissection Cannula Enhanced Version Product Specification, Nov. 4, 1997.
Attachment A PPAQ Approval, Design Review, Design Freeze, Sep. 15, 1997.
Attachment A, Nov. 4, 1997.
McCoy Lab Notebook No. 166, Sep. 5, 1997.
VasoView III Development Team Market Preference Data Sheet, Sep. 4, 1997.
VasoView Big Balloon & Handle Market Preference Data Sheet, Mar. 11, 1997.
VasoView Balloon Dissection Cannula Product Label.
Product Specification History Dissection Tools, Jun. 27, 1996.
Product Specification for VasoView Dissection Tools (Rev date Apr. 15, 1996).
Memo to file re Monthly Program Review Summaries, Jul. 9, 1996.
Memo to Total Heart Team regarding Notes from Assn of PA Annual meeting, Jan. 26, 1996.
Memo re FMEA Rationale for SVH Balloon Dissection Cannula, Jun. 24, 1996.
VasoView Balloon Dissection System Product Label (OMS-BDS).
Manufacturing Process instruction for Balloon Dissection System.
Chin Memo regarding Saphenous Vein Harvesting.
Memo regarding Design Review Path Freeze Criteria OMS-BDS, Jul. 1, 1996.
Product Specification VasoView Balloon Dissection System, Jun. 21, 1996.
VasoView Balloon Dissection System Design Validation Conclusions, Jul. 10, 1996.
VasoView Balloon Dissection System Market Preference Data Sheet, Jul. 2, 1996.
VasoView Procedure Information.
Outstanding Clinical Questions & MPT Data Sheet.
Email regarding Pig Lab Results, Aug. 4, 1995.
Summary of Clinical, Jul. 3, 1996.
AATS meeting Update.
VasoView Balloon Dissection System Market Preference Data Sheet, May 29, 1996.
Chin Letter to FDA regarding Pre-Market notification 510K for Tapered Tip Balloon Dissection Cannula, Jul. 17, 1995.
VasoView Balloon Dissection System Market Release Meeting, Jul. 11, 1996.
WII Team Meeting, Dec. 4, 1996.
Jeffrey Wayne Baxter deposition transcript, Sep. 26, 2008.
Albert Chin deposition transcript, Sep. 10, 2008.
Edwin Hlavka deposition transcript, Sep. 8, 2008.
John Lunsford deposition transcript, Sep. 24, 2008.
Justin Williams deposition transcript, Oct. 8, 2008.
Eric Willis deposition transcript, Oct. 7, 2008.
Responses of Maquet Cardiovascular, L.L.C. To Respondents Terumo Corporation and Terumo Cardiovascular Systems Corporation's Second Set of Requests for Admission, Nov. 3, 2008.
Supplemental Responses of Maquet Cardiovascular, L.L.C. To Respondents Terumo Corporation and Terumo Cardiovascular Systems Corporation's Requests for Admission Nos. 8-56, Nov. 20, 2008.
Responses of Maquet Cardiovascular, L.L.C. To Respondents Terumo Corporation and Terumo Cardiovascular Systems Corporation's Third Set of Request for Admission, Nov. 24, 2008.
Responses of Maquet Cardiovascular L.L.C. To Certain Interrogatories from Respondents Terumo Corporation and Terumo Cardiovascular Systems Corporation's First Set of Interrogatories [Nos. 3, 5, 7, 12, 23, 45, 48, 49, 59, 62, and 69], May 23, 2008.
Responses of Maquet Cardiovascular L.L.C. To Respondents Terumo Corporation and Terumo Cardiovascular Systems Corporation's First Set of Interrogatories [Nos. 1-78], Jun. 6, 2008.
Supplemental Responses of Maquet Cardiovasular L.L.C. To Respondents Terumo Corporation and Terumo Cardiovascular Systems Corporation's Interrogatory Nos. [5, 6, 8, 14, 32, 33 & 67], Jul. 23, 2008.
Supplemental Responses of Maquet Cardiovascular L.L.C. To Respondents Terumo Corporation and Terumo Cardiovascular Systems Corporation's Interrogatory No. 21, Sep. 5, 2008.
Responses of Maquet Cardiovascular L.L.C. To Respondents Terumo Corporation and Terumo Cardiovascular Systems Corporation's Systems Corporation's Third Set of Interrogatories [Nos. 87-115], Aug. 6, 2008.
Responses of Maquet Cardiovascular L.L.C. To Respondents Terumo Corporation and Terumo Cardiovascular Systems Corporation's Fourth Set of Interrogatories [Nos. 116-148], Aug. 11, 2008.
Supplemental Responses of Maquet Cardiovascular L.L.C. To Respondents Terumo Corporation and Terumo Cardiovascular Systems Corporation's Fourth Set of Interrogatories, Sep. 12, 2008.
Second Supplemental Responses of Maquet Cardiovascular L.L.C. To Respondents Terumo Corporation and Terumo Cardiovascular Systems Corporation's Interrogatory Nos. 130, 131, 133, 134, 136 & 137, Oct. 21, 2008.
Supplemental Response of Maquet Cardiovascular L.L.C. To Respondents Terumo Corporation and Terumo Cardiovascular Systems Corporation's Interrogatory Nos. 146 & 148, Oct. 31, 2008.
Responses of Maquet Cardiovascular L.L.C. To Respondents Terumo Corporation and Terumo Cardiovascular Systems Corporation's Fifth Set of Interrogatories [Nos. 149-152], Sep. 5, 2008.
Responses of Maquet Cardiovascular L.L.C. To Respondents Terumo Corporation and Terumo Cardiovascular Systems Corporation's Sixth Set of Interrogatories [Nos. 153-155], Sep. 10, 2008.
Responses of Maquet Cardiovascular L.L.C. To Respondents Terumo Corporation and Terumo Cardiovascular Systems Corporation's Seventh Set of Interrogatories, Nov. 21, 2008.
Responses of Maquet Cardiovascular L.L.C. To Respondents Terumo Corporation and Terumo Cardiovascular Systems Corporation's Eighth Set of Interrogatories, Nov. 24, 2008.

(56) References Cited

OTHER PUBLICATIONS

MacKenzie, The Use of Laryngoscope in Diseases of the Throat: with an essay on Hoarseness Loss of Voice, and Stridulous Breathing, in Relation to Nervo-Muscular Affection of the Larynx (1869).
Schwyzer, "On Bronchoscopy. With Report of a Case in Which a Foreign Body was Removed from the Right Lower Lobe of a Lung Through a Bronchoscope", Read before the Minnesota Academy of Medicine pp. 194-206 (Dec. 2, 1903).
Mathews, A Treatise on Diseases of the Rectum, Anus, and Signoid Flexure (1903).
Mayo, "The Surgical Treatment of Varicose Veins", The St. Paul Medical Journal, vol. VI, pp. 695-699 (1904).
Fenwick, "A Handbook of Clinical Electric-Light Cystoscopy" (1905).
Carrel et al.., "Uniterminal and Biterminal Venous Transplantations", Surgery, Gynecology and Obstetrics, vol. II, pp. 266-286 (1906).
Mayo, "Treatment of Varicose Veins", Surgery, Gynecology and Obstetrics, pp. 385-388 (1906).
Carrel et al., "Results of the Biterminal Transplantation of Veins", pp. 415-422 (1906).
Jackson, "Endothelioma of the Right Bronchus Removed by Peroral Bronchoscopy", The American Journal of the Medical Sciences, vol. CLIII, pp. 37-375 (1917).
Stern, "Resection of Obstruction at the Vesical Orifice; New Instruments Resectotherm; Resectoscope and New Method", Journal of American Medical Assoction, vol. 87, No. 21, pp. 1726-1730 (1926).
Chandler, "Internal Pneumolysis: Results of 110 Consecutive Operations", the Lancet, pp. 879-882 (Oct. 19, 1935).
Hurley, "Some Practical Guiding Principles for Closed Pneumonolysis", Canad: M.A.J., vol. 56, pp. 625-627 (Jun. 1947).
Bayliss, "Closed Intrapleural Pneumonolysis", Chest, vol. XIII, pp. 479-515 (1947).
Sarot et al., "Closed Pneumonolysis (Enucleation Technique)", Chest, vol. XVI, No. 5, pp. 509-542 (Nov. 1949).
Morris et al., "Arterial Bypass Below the Knee", Surgery, Gynecology & Obstetrics, vol. 108, pp. 321-332 (Jan.-Jun. 1959).
Hall, "The Great Saphenous Vein Used in Situ as an Arterial Shunt After Extirpation of the Vein Valves", Surgery, vol. 51. No. 4, pp. 492-495 (Apr. 1962).
Linton et al., "Autogenous Saphenous Vein Bypass Grafts in Femoropopliteal Obliterative Arterial Disease", Surgery, vol. 51, No. 1, pp. 62-73 (Jan.-Jun. 1962).
Palva, "Mediastinoscopy—A New Field for Bronchologists", Acta Oto-Laryngologica, vol. 53, Issue 2 & 3 (1961), http://www.informaworld.com/smpp/content.
Lore, "Tender Grip Forceps", The American Journal of Surgery, vol. 104, pp. 84-85 (Jul. 1962).
May et al., "Arterialized in Situ Saphenous Vein", Archives of Surgery, vol. 91, No. 5, pp. 743-750 (Nov. 1965).
Steptoe, "Abdominal Laparoscopy", Laparoscopy in Gynaecology, pp. 13-25 (1967).
Favaloro, "Saphenous Vein Graft in the Surgical Treatment of Coronary Artery Disease", The Journal of Thoracic and Cardiovascular Surgery, vol. 58, No. 2, (Aug. 1969).
Samuels et al., "In Situ Saphenous Vein Arterial Bypass: A Study of the Anatomy Pertinent to its Use in Situ as a Bypass Graft with a Description of a New Venous Valvulatome", The American Surgeon, vol. 34, No. 2, pp. 122-130 (Feb. 1968).
Barner et al., "Late Failure of Arterialized in Situ Saphenous Vein", Archives of Surgery, vol. 99, pp. 781-786 (Dec. 1969).
Effler et al., "The Simple Approach to Direct Coronary Artery Surgery", The Journal of Thoracic and Cardiovascular Surgery, vol. 62, No. 4, pp. 503-510 (Oct. 1971).
Nagovitsyn, "Varicocide Treatment of Varicose Veins of the Lower Extremities" (1971).
Koontz et al., "Factors Influencing Patency of the Autogenous Vein-Femoropoliteal Bypass Grafts: An Analysis of 74 Cases", Surgery, vol. 71, No. 5, pp. 753-759 (May 1972).

Rizk et al., "Vascular Endoscopy", Radiology, vol. 106, No. 1, pp. 33-35 (Jan. 1973).
Balasegaram, "Hepatic Surgery: A Review of a Personal Series of 95 Major Resections", The Australian and New Zealand Journal of Surgery, vol. 42, No. 1, pp. 1-10 (Aug. 1972).
Brody et al., "Changes in Vein Grafts Following Aorto-Coronary Bypass Induced by Pressure and. Ischemia", The Journal of Thoracic and Cardiovascular Surgery, vol. 64, No. 6, pp. 847-854 (Dec. 1972).
Jones et al., "Lesions Observed in Arterial Autogenous Vein Grafts", Cardiovascular Surgery, pp. 198-210 (1972).
Kern et al., "The Intimal Proliferation in Aortic—Coronary Saphenous Vein Grafts: Light and electron microscopic studies", American Heart Journal, pp. 771-777 (Dec. 1972).
Crispin et al., "Intravascular Observation and Surgery Using the Flexible Fibrescope", The Lancet, pp. 750-751 (Apr. 7, 1973).
Abbott et al., "Structural Changes During Preparation of Autogenous Venous Grafts", Surgery, vol. 76, No. 6, pp. 1031-1040 (Dec. 1974).
Brook, "A historical review of the histology of patent autogenous vein grafts and vein patches", The Journal of Cardiovascular Surgery, vol. 16, No. 1, pp. 43-52 (Jan.-Feb. 1975).
Shepherd et al., "Physical Characteristics of Venous System in Man", Veins and their Control, pp. 171-172 (1975).
Gittes, "Operative Nephroscopy", J Urol. (Aug. 1976), http://www.ncbi.nlm.nih.gov/sites/entrez.
Cutler et al., "Autologous Saphenous vein femoropopliteal bypass: Analysis of 298 cases", Surgery, vol. 79, No. 3, pp. 325-331 (Mar. 1976).
Lukomsky et al., "Diagnosing Phasic Nature of Pulmonary Carcinoma by Means of Combined MediastinoLaparoscopy" 1976.
Corson, "Chapter 10: Operating Room Preparation and Basic Techniques", Laparoscopy, pp. 88-102 (1977).
Gottlob, The preservation of the venous endothelium by <.
Tarlovskaya et al., "Endoscopic Investigations for Determining Lung Cancer Stage" (1978).
Stiles, "Technique of Saphenous vein aorta-coronary bypass grafting", The Journal of Thoracic and Cardiovascular Sugery, vol. 78, No. 2, pp. 305-308 (Aug. 1979).
May et al., "Concluding Remarks on the Therapy of Incompetent Perforating Veins", Perforating Veins, pp. 251-253 (1981).
Szilagyi et al., "Autogenous vein grafting in femoropopliteal atherosclerosis:the limits of its effectiveness", Surgery, vol. 86, No. 6, pp. 836-851 (1979).
Flemma et al., "Complications of Aortocoronary Bypass Grafting", Complications of Intrathoracic Surgery, pp. 167-177 (1979).
Ochsner et al., "The Internal Mammary Artery as a Coronary Artery Bypass Graft", Coronary Heart Surgery, pp. 120-124 (1979).
Buxton et al., "The significance of vein wall thickness and diameter in relation to the patency of femoropopliteal Saphenous vein bypass grafts", Surgery, vol. 87, No. 4, pp. 425-431 (Apr. 1980).
Hofer et al., "Morphologic Studies in Saphenous Vein Grafts for Aorto-coronary Bypass Surgery Part 1: Morphology of the Graft Using Ordinary Surgical Preparation Techniques", The Thoracic and Cardiovascular Surgeon, vol. 29, No. 1, pp. 32-37 (1981).
Bonchek, "Prevention of endothelial damage during preparation of Saphenous veins for bypass grafting", The Journal of Thoracic and Cardiovascular Surgery, vol. 79, No. 6, pp. 911-915 (Jun. 1980).
McGeachie et al. "Vein to Artery Grafts: A Quantitative Study of Revascularization by Vasa Vasorum and its Relationship to Intimal Hyperplasia", Annals of Surgery, vol. 194, No. 1, pp. 100-107 (Jul. 1981).
Gundry et al., "Intraoperative Trauma to Human Saphenous Veins: Scanning Electron Microscopic Comparison of Preparation Techniques", The Annals of Thoracic Surgery, vol. 30, No. 1, pp. 40-47 (Jul. 1980).
Buchbinder et al., "Comparison of Patency Rate and Structural Change in In Situ and Reversed Vein Arterial Bypass", Journal of Surgical Research, vol. 30, No. 3, pp. 213-222 (Mar. 1981).
Gundry et al., "Optimal preparation techniques for human Saphenous vein grafts", Surgery, vol. 88, No. 6, pp. 785-794 (Dec. 1980).
Moser, "Angioscopic Visualization of Pulmonary Emboli", Chest, vol. 77, No. 2, pp. 198-201 (Feb. 1980).
Ford et al., "Isolation of Adult Canine Venous Endothelium for Tissue Culture", in Vitro, vol. 17, No. 1, pp. 44-50 (Jan. 1980).

(56) References Cited

OTHER PUBLICATIONS

Delaria et al., "Leg wound complications associated with coronary revascularization", The Journal of Thoracic and Cardiovascular Surgery, vol. 81, pp. 403-407 (1981).
Fogarty et al.., "Adjunctive Intraoperative Arterial Dilation: Simplified Instrumentation Technique", Archives of Surgery, vol. 116, No. 11, pp. 1391-1398 (Nov. 1981).
Logerfo et al., "An improved technique for preservation endothelial morphology in vein grafts", Surgery, vol. 90, No. 6, pp. 1015-1024 (Dec. 1981).
Greenberg et al., "Vein-Donor-Leg Cellulities After Coronary Artery Bypass Surgery", Annals of Internal Medicine, vol. 97, No. 4, pp. 565-566 (Oct. 1982).
Gunstensen et al., "Intimal Hyperplasia in Autogenous Veins Used for Arterial Replacement", The Canadian Journal of Surgery, vol. 25, No. 2, pp. 158-165 (Mar. 1982).
Mcgoon, "Incision Decision Advertisement", The Journal of Thoracic and Cardiovascular Surgery, vol. 83, No. 5 (May 1982).
Catinella et al.., "The factors influencing early patency of coronary artery bypass vein grafts: Correlation of angiographic and ultrastructure findings", The Journal of Thoracic Cardiovascular Surgery, vol. 83, No. 5, pp. 686-700 (May 1982).
Feikes et al., "Harvesting and protection of the Saphenous vein associated with early delivery of blood cardioplegia in coronary artery bypass graft surgery", American Heart Journal, vol. 104, No. 2, Part 1, pp. 329-332 (1982).
Leather et al., "The in Situ Saphenous Vein for Arterial Bypass", Biologic and Synthetic Vascular Prostheses, pp. 351-364 (1982).
Sottiurai et al., "Autogenous Vein Grafts: Experimental Studies", Biologic and Synthetic Vascular Prostheses, pp. 311-364 (1982).
Kinney et al., "Transluminal Angioplasty: A Mechanical-Pathophysiological Correlation of its Physical Mechanisms", Radiology, vol. 153, No. 1, pp. 85-89 (Oct. 1984).
Teimourian et al., "Subcutaneous Endoscopy in Suction Lipectomy", Plastic and Reconstructive Surgery, vol. 74, No. 5, pp. 708-711 (Nov. 1984).
Gregory et al., "Composite Grafts: An Alternative to Saphenous Vein for Lower Extremity Arterial Reconstruction", the Journal of Cardiovascular Surgery, vol. 24, No. 1, pp. 53-57 (Jan.-Feb. 1983).
Hufnagel, "Chapter 1: History of Vascular Grafting", Vascular Grafting—Clinical Appliations and Techniques, pp. 1-12 (1983).
Shah et al., "In Situ Saphenous Vein Arterial Bypass", Vascular Grafting: Clinical Applications and Techniques, pp. 133-147 (1983).
Baddour et al., "Recurrent Cellulitis After Coronary Bypass Surgery", The Journal of the American Medical Journal, vol. 251, No. 8, pp. 1049-1052 (Feb. 17, 1984).
Chin Et Al., "A Physical Measurement of the Mechanisms of Transluminal Angioplasty", Surgery, vol. 95, No. 2, pp. 196-201 (Feb. 1984).
Crew et al., "Carotid Surgery without Angiography", The American Journal of Surgery, vol. 148, pp. 217220 (Aug. 1984).
Adcock et al., "Optimal Techniques for Harvesting and Preparation of Reversed Autogenous Vein Grafts for Use as Arterial Substitutes: a Review ", vol. 96, No. 5. (Nov. 1984).
Rashid et al., "Subcutaneous Technique for Saphenous Vein Harvest", The Annals of Thoracic Surgery, vol. 37, No. 2, pp. 169-170 (Feb. 1984).
Ben-Simhon et al, "Vein Harvesting by Long Blunt and Blind Dissection. A Standardized Technique in the Dog", Biomaterials, Medical Devices, and Artificial Organs, vol. 12, No. 1 & 2, pp. 51-66 (1984).
Dorsey, "Harvesting the Greater Saphenous Vein with a Subcutaneous Vein Remover", The Canadian Journal of Surgery, vol. 28, No. 1, pp. 13-14 (Jan. 1985).
Tilanus et al., "Saphenous Vein or Ptfe for Femoropopliteal Bypass", Annals of Surgery, vol. 202, No. 6, pp. 780-782 (Dec. 1985).
Dorsey, "Saphenous Vein Harvesting Using a Subcutaneous Vein Remover", Minnesota Medical Association, pp. 195-198 (Mar. 1985).
Baddour, "Delayed Soft Tissue Infections in Saphenous Venectomy Limbs of Coronary Bypass Patients", Infections in Surgery, vol. 4, No. 4, pp. 243-248 (Apr. 1985).
Spears et al., "Coronary Angioscopy During Cardiac Catheterization", Journal of the American College of Cardiology, vol. 6, No. 1, pp. 93-97 (Jul. 1985).
Hulka et al., "Standard Gynecologic Techniques", Textbook of Laparoscopy, (1994).
Hobbs, "A New Approach to Short Saphenous Vein Varicosities", Surgery of Veins, pp. 301-321 (1985).
Nagovitsyn, "Operative Treatment of Acute Thromophlebitis of the Superficial Veins of the Lower Extremities" (1985).
Weaver et al., "The Lesser Saphenous Vein: Autogenous Tissue for Lower Extremity Revascularization", Journal of Vascular Surgery, vol. 5, No. 5, pp. 687-692 (May 1987).
Scher et al., "Prevention and Management of Ischemic Complications of Vein Harvest Incisions in Cardiac Surgery Case Reports", Angiology, the Journal of Vascular Diseases, vol. 37, No. 1, pp. 119-123 (Jan. 1986).
Taylor et al., "Present Status of Reversed Vein Bypass for Lower Extremity", Journal of Vascular Surgery, vol. 3, No. 2, pp. 288-297 (Feb. 1986).
Meldrum-Hanna, "Long Saphenous Vein Harvesting", The Australian and New Zealand Journal of Surgery, vol. 56, No. 12, pp. 923-924 (Dec. 1986).
Raess et al., "Lesser Saphenous Vein as an Alternative Conduit of Choice in Coronary Bypass Operations", The Annals of Thoracic Surgery, vol. 41, No. 3, pp. 334-336 (Mar. 1986).
Sanborn, "Vascular Endoscopy: Current State of the Art", British Medical Bulletin, vol. 42, No. 3, pp. 270273 (Apr. 19861.
Grundfest et al., "The Current Status of Angioscopy and Laser Angioplasty", Journal of Vascular Surgery, vol. 5, No. 4, pp. 667-673 (Apr. 1987).
Classen et al., "The Impact of Endoscopy", Gastroenterological Endoscopy, pp. 23-26.
Lemaitre et al., "In Situ Grafting Made Easy", Archives of Surgery, vol. 123, No. 1, pp. 101-103 (Jan. 1988).
Fleisher et al, "Angioscopically Monitored Saphenous Vein Valvulotomy", Journal of Vascular Surgery, vol. 4, No. 4, pp. 360-364 (Oct. 1986).
Miller, "Endoscopic Surgery of the Upper Urinary Tract", British Medical Bulletin, vol. 43, No. 3, pp. 274-279 (1986).
Nagovitsyn, "The Endoscopic Correction of the Shin Venous Blood Flow", Vestnik Khriurgii, vol. 137, No. 11, pp. 48-51 (Nov. 1986).
Noera et al., "Microscopic Evaluation in Saphenous Veins Used as Aortocoronary Bypass Grafts", Giornale Italiano di Cardiologia, vol. 16, No. 12, pp. 1037-1042 (Dec. 1986).
Suma et al. "Vein Perfusions System" for Harvesting the Saphenous Vein Graft in Coronary Bypass Surgery, Kyobu Geka, vol. 39, No. 8, pp. 622-623 (Aug. 1986).
Mehigan, "Symposium: Vascular Application of Angioscopy and Lasers", Journal of Vascular Surgery, vol. 5, No. 4, pp. 664-666 (Apr. 1987).
Taylor et al., "Autogenous Reversed Vein Bypass for Lower Extremity Ischemia in Patients with Absent of Inadequate Greater Saphenous Vein", The American Journal of Surgery, vol. 153, pp. 505-510 (May 1987).
Hashizume et al., "Intimal Response of Saphenous Vein to Intraluminal Trauma by Simulated Angioscope Insertion", Journal of Vascular Surgery, vol. 5, No. 6, pp. 862-868 (Jun. 1987).
Spyt, "Harvesting of the Lesser Saphenous Vein", The Annals of Thoracic Surgery, vol. 43, No. 6, p. 691 (Jun. 1987).
White, "Angioscopy and Laser in cardiovascular Surgery: Current Applications and Future Prospects", Aust. N. Z. J. Surg., vol. 58, No. 271-274 (1988).
Matsumoto et al., "Direct Vision Valvulotomy in in Situ Venous Bypass", Surgery Gynecology & Obstetrics, vol. 165, No. 4 (Oct. 1987).
Classen et al., "Electronic Endoscopy—The Latest Technology", Endoscopy, vol. 19, pp. 118-123 (1987).
Delmotte, "The Electronic Video Endoscope of Tomorrow, but First, its Present Status", Acta Endoscopica, vol. 17, No. 2, pp. 89-91 (1987).

(56) References Cited

OTHER PUBLICATIONS

Dimitri et al., "A Quick and Atraumatic Method of Autologous Vein Harvesting Using the Subcutaneous Extraluminal Dissector", the Journal of Cardiovascular Sugery, vol. 28, No. 2, pp. 103-111 (Mar.-Apr. 1987).
Secroun, "Future Methods of Endoscopy", Acta Endoscopica, vol. 17, No. 2, pp. 92-95 (1987).
Lannerstad et al., "Effects of Different Graft Preparation Techniques on the Acute Thrombogenicity of Autologous Vein Grafts", European Surgical Research, vol. 19, pp. 395-399 (Nov.-Dec. 1987).
Towne, "Vascular Endoscopy", Perioperative Assessment in Vascular Surgery, pp. 303-313 (1987).
Chin et al., "The Effect of Valvulotomy on the Flow Rate Through the Saphenous Vein Graft: Clinical Implications", Journal of Vascular Surgery, vol. 8, No. 3, pp. 316-320 (Sep. 1988).
Wood, "Locating Previously "Stripped" Venous Systems and Harvesting of Lesser Saphenous Vein", The Annals of Thoracic Surgery, vol. 45, No. 3 (Mar. 1988).
Takemoto, "Electronic Endoscopy: Its Present and Future", Journal of Gastroenterology and Hepatology, vol. 4, pp. 75-80 (1989).
Cardella et al., "Lower-Extremity Venous Thrombosis: Comparison of Venography, Impedance Plethysmography, and Intravenous Manometry", Radiology, vol. 168, No. 1, pp. 109-112 (Jul. 1988).
Citrin et al., "Replacement of the Carotid Artery Using Nonreversed Saphenous Vein", Surgery, Gynecology & Obstetrics, vol. 167, pp. 155-157 (Aug. 1988).
Woelfle et al., "Intraoperative Assessment of in Situ Saphenous Vein Bypass Grafts by Vascular Endoscopy", European Journal Vascular Endovascular Surgery European, vol. 2, pp. 257-262 (Aug. 1988).
Patel et al., "The Use of Fiber-Optic Intraluminal Transillumination for Saphenous Vein Harvesting", Journal of Vascular Surgery, vol. 8, No. 3, pp. 346-348 (Sep. 1988).
Gaudiani et al., "An Improved Technique for the Internal Mammary Artery Coronary Bypass Graft Procedure", Journal of Cardiac Surgery, vol. 3, No. 4, pp. 467-473 (Dec. 1988).
Hauer et al., "Endoscopic Subfascial Dissection of Perforating Veins", Surgical Endoscopy, vol. 2, pp. 512 (1988).
Lee et al., "Hazards of Angioscopic Examination: Documentation of Damage to the Arterial Intima", American Heart Journal, vol. 116, No. 6, pp. 1530-1536 (Dec. 1988).
Rey et al., "Electronic Video Endoscopy: Preliminary Results of Imaging Modification", Endoscopy, vol. 20, pp. 8-10 (1988).
Taylor et al., "Reversed vs. In Situ: Is Either the Technique of Choice for Lower Extremity Vein Bypass?", Perspectives in Vascular Surgery, vol. 1. No. 1, pp. 35-59 (1988).
Barnes et Al., "Technical Innovations in Nonreversed Translocated Saphenous Vein Bypass", Journal of Vascular Surgery, vol. 9, No. 3, pp. 499-501 (Mar. 1989).
Chin et al, "Technique Using the Fiberoptic Valvulotome for the in Situ Vein Graft", Surgery Gynecology & Obstetrics, vol. 169, No. 3, pp. 255-256 (Sep. 1989).
Hauer, "Diagnosis and surgical management of varicosities", Herz, vol. 14, No. 5, pp. 274-282 (1989).
Fogarty et al., "Combined Thrombectomy and Dilation for the Treatment of Acute Lower Extremity Arterial Thrombosis", Journal of Vascular Surgery, vol. 10, No. 5, pp. 531-534 (Nov. 1989) a1989-11.
Burnand, "Reversed Saphenous Vein for Femoropopliteal Bypass Grafting", Vascular Surgical Techniques an Atlas, pp. 228-234 (1989).
Chin et al., "Angioscopic Preparation for Saphenous Vein in Situ Bypass Grafting", Endovascular Surgery, pp. 74-81 (1989).
Lavee et al., "Complications of Saphenous Vein Harvesting Following Coronary Artery Bypass Surgery", The Journal of Cardiovascular Surgery, vol. 30, No. 6, pp. 989-991 (1989).
Utley et al., "Preoperative Correlates of Impaired Wound Healing After Saphenous Vein Excision", The Journal of Cardiovascular Surgery, vol. 98, No. 1, pp. 147-149 (1989).
Veith et al., Short Vein Grafts in Limb-saving Arterial Reconstructions, Journal of Vascular and Interventional Radiology, vol. 1, No. 1, pp. 57-61 (Nov. 1990).
Louagie et al., "Viability of Long-Term Cryopreserved Human Saphenous Vein", The Journal of Cardiovascular Surgery, vol. 31, No. 1, pp. 92-100 (Jan.-Feb. 1990).
Galloway, Jr. et al, "A new Device for Interactive, Image- Guided Surgery", Medical Imaging V: Image Capture, Formatting, and Display, Spie—The International Society of Optical Engineering (Feb. 1991).
Myers et. al., "Semi-closed, ex-situ, non-reversed or reversed autogenous vein grafting", The Journal of Cardiovascular Surgery, vol. 32, No. 1, pp. 110-116 (Jan.-Feb. 1991).
Bailey et al., "Laparoscopic Cholecystectomy: Experience with 375 Consecutive Patients", Ann. Surg., vol. 214, No. 4, pp. 531-540 (1991).
The Southern Surgeons Club, "A Prospective Analysis of 1518 Laparoscopic Cholecystectomies", New England Journal of Medicine, vol. 324, pp. 1073-1078 (Apr. 18,1991).
Clayman et al.., "Laparoscopic Nephrectomy", the New England Journal of Medicine, vol. 324, No. 19, pp. 1370-1371 (May 9, 1991).
Lam, et al., "Surgical Procedures for Uncomplicated ("Routine") Female Stress Incontinence", The Urologic Clinics of North America, vol. 18, No. 2, pp. 327-337 (May 1991).
Couto et al., "Endoscopic ligation of perforator leg veins", The Lancet, vol. 337, p. 1480 (Jun. 15, 1991).
Milgalter et al., "A technique to harvest the inferior epigastric arteries for coronary bypass procedures", Journal of Cardiac Surgery, vol. 6, No. 2, pp. 306-310 (Jun. 1991).
Preising et al., "A Literature Review: Robots in Medicine", —Engineering in Medicine and Biology (Jun. 1991).
Owen et al., "Endoscopic ligation of perforator leg veins", Lancet, vol. 338, p. 248 (Jul. 27, 1991).
Mccollum et al., "A Simple Means of Access for Harvesting the Lesser Saphenous Vein", European Journal Vascular Endovascular Surgery, vol. 5, pp. 469-470 (Aug. 1991).
Feldman, "Laparoscopic Nephrectomy", Journal of Medicine, vol. 325, No. 15, pp. 1110-1111 (Oct. 10, 1991).
Nowzaradan et al., "Laparoscopic Appendectomy for Acute Appendicitis: Indications and Current Use", Journal of Laparoendoscopic Surgery, vol. 1, No. 5, pp. 247-257 (Oct. 1991).
Spaw et al., "Laparoscopic Hernia Repair: The Anatomic Basis", Journal of Laparoendoscopic Surgery, vol. 1, No. 5, pp. 269-277 (Oct. 1991).
Stierli et al., "In Situ Femorodistal Bypass: Novel Technique for Angioscope-Assisted Intraluminal Side-Branch Occlusion and Valvulotomy. A preliminary Report", British Journal of Surgery, vol. 78, No. 11, pp. 1376-1378 (Nov. 1991).
Bailey et al., "Combined Laparoscopic Cholecystectomy and Selective Vagotomy", Surgical Laparoscopy & Endoscopy, vol. 1, No. 1, pp. 45-49 (1991).
Bergamini et al., "Experience with in situ saphenous vein bypass during 1981 to 1989:Determinant factors of long-term patency", p. 137 (1991).
Corbitt, Jr., "Laparoscopic Hemiorrhaphy", Surgical Laparoscopy & Endoscopy, vol. 1, No. 1, pp. 23-25 (1991).
Cuschieri, "Variable curvature shape-memory spatula for laparoscopic surgery", Surgical Endoscopy, vol. 5, pp. 179-181 (1991).
Fitzgibbons et al., "Open Laparoscopy", Surgical Laparoscopy, pp. 87-97 (1991).
Fowler et al.., "Laparoscopy-Assisted Sigmoid Resection", Surgical Laparoscopy & Endoscopy, vol. 1, No. 3, pp. 183-188 (1991).
Gazayerli, "The Gazayerli Endoscopic Retractor* Model 1" Surgical Laparoscopy & Endoscopy, vol. 1, No. 2, pp. 98-100 (1991).
Zhila et al., "High Resection of the Left Testicular Vein and Ligation of the Internal Iliac Arteries by Means of Retroperitoneoscope", No. 5 (1991).
Zucker, "Laparoscopic Guided Cholecystectomy With Electrocautery Dissection", Surgical Laparoscopy, pp. 143-182 (1991).
"3rd World Congress of Endoscopic Surgery" (Jun. 18-20, 1992).
Santilli et al., "Comparison of Preoperative Standard Angiography with Preoperative Balloon Occlusion Femoral Angiography of the Lower Extremity", Journal of Investigative Surgery, vol. 6, No. 1, pp. 83-95 (Feb. 1993).

(56) References Cited

OTHER PUBLICATIONS

Zucker, Surgical Laparoscopy Update, pp. 59-61 (1993).
Wittens et al., "A New Closed" in Situ Vein Bypass Technique, European Journal Vascular Endovascular Surgery, vol. 8, pp. 166-170 (1994).
Biglioli et al., "Arterial and Venous Graft Utilization in Reoperative Coronary Artery Surgery", Cardiology and Cardiac Surgery: Current Topics, pp. 399-415 (1993).
Chin et al., "Novel Technique and Instrumentation for Laparoscopic Application of Hemostatic Clips", The Journal of the American Association of Gynecologic Laparoscopists, vol. 1, No. 2, pp. 150-153 (Feb. 1994).
Chin et al., "Gasless Laparoscopy Using a Planar Lifting Technique", Journal of the American College of Surgeons, vol. 178, No. 4, pp. 401-403 (Apr. 1, 1994).
Kavoussi et al., "Telerobotic Assisted Laparoscopic Surgery: Initial Laboratory and Clinical Experience", Urology, vol. 44, No. 1, pp. 15-19 (Jul. 1994).
Van Dijk et al., A New "Closed" in Situ Vein Bypass Technique Results in a Reduced Wound Complication Rate, European Journal Vascular Endovascular Surgery, vol. 10, pp. 162-167 Aug. 1995).
Lumsden et al., "Subcutaneous, Video-Assisted Saphenous Vein harvest: Report of the first 30 Cases", Cardiovascular Surgery, vol. 4, No. 6, pp. 771-776 (Dec. 1996).
Tighe, Instrumentation for the Operating Room: A Photographic Manual (1994).
Dion et al., "Experimental laparoscopic aortobifemoral bypass", Surgical Endoscopy, vol. 9, pp. 894-897 (1995).
Bowersox et al., "Vascular applications of telepresence surgery: Initial feasibility studies in swine", Journal of Vascular Surgery, vol. 23, No. 2., pp. 281-287 (Feb. 1996).
Rosenthal, "Endoscopic in Situ Bypass", The Surgical Clinics of North America, vol. 75, No. 4, pp. 703-713 (Aug. 1995).
Nwasokwa et al., "Coronary Artery Bypass Graft Disease", Annals of Internal Medicine, vol. 123, No. 7, pp. 528-545 Oct. 1995).
Davies et al., "Pathophysiology of Vein Graft Failure: a Review", European Journal Vascular Endovascular Surgery, vol. 9, pp. 7-18 (1995).
Gelijns et al., "From the Scalpel to the Scope: Endoscopic Innovations in Gastroenterology, Gynecology, and Surgery", Sources of Medical Technology: Universities and Industry, vol. V, pp. 67-96 (1995).
Lumsden et al., "Vein Harvest", Endoscopic Plastic Surgery (1995).
Sawaizumi et al., "Endoscopic Microsurgical Anastomosis: Experimental Study of microsurgical anastomosis using an endoscope", Journal of Japan Society of Plastic and Reconstructive Surgery, vol. 15, No. 12, pp. 871-879 (1995).
Tebbetts, Tebbetts Endoplastic Instrument System (1995).
Cusimano, "Minimally Invasive Cardiac Surgery for Removal of the Greater Saphenous Vein", Canadian Journal of Surgery, vol. 39 (Oct. 1996), http://www.cma.ca/index.cfm/ci.
Tevaearai et al., "Minimally Invasive Harvest of the Saphenous Vein for Coronary Artery Bypass Grafting", The Annals of Thoracic Surgery, vol. 63, pp. S119-S121 (1997).
Iafrati et al., "Endoscopic in situ bypass: A gentler dissection", Surgical Endoscopy, vol. 12, pp. 463-465 (1998).
Hannah et al., "Laparoscopic Retropubic Urethropexy", The Journal of the American Association of Gynecologic Laparoscopists, vol. 4, No. 1, pp. 47-52 (Nov. 1996).
EndoCABG System: Innovative instrumentation for endoscopic coronary artery bypass grafting (1996).
Lumsden et al., "Subcutaneous, video-assisted saphenous vein harvest", Perspectives in Vascular Surgery, vol. 7, No. 2, pp. 43-55 (1994).
Allen et al., "Endoscopic Saphenous Vein Harvesting", pp. 265-266 (1997).
McCarthy et al, "Tricuspid Valve Repair with the Cosgrove-Edwards Annuloplasty System", The Annals of Thoracic Surgery, vol. 64, pp. 267-268 (1997).
Jordan et al., "Video-assisted saphenous vein harvest: The evolution of a new technique", Journal of Vascular Surgery, vol. 26, No. 3, pp. 405-414 (Sep. 1997).
Moazami, "Minimally Invasive Greater Saphenous Vein Harvesting for Coronary Artery Bypass Surgery", Surgical Rounds, pp. 94-98 (Mar. 1997).
Johnson et al., "Endoscopic Femoral-Popliteal/Distal Bypas Grafting: a Preliminary Report", Journal of American College of Surgeons, pp. 331-336 (1998).
Pierik et al., "Endoscopic versus open subfacial division of incompetent perforating veins in the treatment of venous leg ulceration: A randomized trial", Journal of Vascular Surgery, vol. 26, No. 6, pp. 1049-1054 (1997).
Davis et al., "Endoscopic Vein Harvest for Coronary Artery Bypass Grafting: Technique and Outcomes", The Journal of Thoracic and Cardiovascular Surgery, vol. 116, No. 2, pp. 228-235(Aug. 1998).
Hallock et al., "An Endoscopic Subcutaneous Dissector for Obtaining Vein Grafts", Annals of Plastic Surgery, vol. 41, No. 6, pp. 595-599 (Dec. 1998).
Morris et al., "Minimally Invasive Saphenous Vein Harvesting", The Annals of Thoracic Surgery, vol. 66, pp. 1026-1028 (1998).
Allen et al., "Endoscopic Versus Traditional Saphenous Vein Harvesting: A Prospective, Randomized Trial", pp. 26-31 (1998).
Stavridis et al., "Minimally Invasive Long Saphenous Vein Harvesting Using a Laryngoscope", The Heart Surgery Forum, vol. 1, pp. 37-40 (Jan. 30, 1998).
Tran et al., "Tunneling versus open harvest technique in obtaining venous conduits for coronary bypass surgery", European Journal of Cardo-thoracic Surgery, vol. 14, pp. 602-606 (1998).
Wilson, "Ethicon Endopath System", Minimally Invasive Vein Harvesting the Second Generation (Jun. 1998).
"Resins Aid in Bypass Surgery", Plastics Engineering, vol. Liv, No. 8 (Aug. 1998).
Dregelid et al., "Endothelial cell injury in human saphenous veins after manipulation and tweezer grasping", Journal of Cardiovascular Surgery, vol. 29, pp. 464-469 (1988).
Voellinger et al, "Video-Assisted Vein Harvest: a Single Institution's Experience of 103 Peripheral Bypass Cases", Vascular Surgery, vol. 32, No. 6, pp. 545-557 (Nov./Dec. 1998).
Akbari et al., "Saphenous Vein Bypass to Pedal Arteries in Diabetic Patients", pp. 227-232 (1998).
Belkin et al., "Nonreversed Saphenous Vein Bypass for Infrainguinal Arterial Reconstruction", Techniques in Vascular and Endovascular Surgery, pp. 233-241 (1998).
Kulbaski et al., "Video-Assisted Saphenous Vein Harvest", Techniques in Vascular and Endovascular Surgery, pp. 91-102 (1998).
Kyo et al., "Endoscopic harvest of saphenous vein graft for coronary artery bypass grafting: Saitama—Olympus technique", European Journal of Cardio-thoracic Surgery, vol. 14, Supp. 1, pp. S94-S99 (1998.
Lacroix et al., "Classic versus Endoscopic Perforating Vein Surgery: A Retrospective Study", Acia chir bieg, vol. 98, pp. 71-75 (1998).
Stoney et al., "Lower Extremity", Comprehensive Vascular Exposures, pp. 145-182 (1998).
Brown et al., "Heparin Reduced Residual Clot Within the Lumen of Endoscopically Harvested Saphenous Veins", http://www.aats.org/annualmeeting/Abstracts/2007/T7.html (Aug. 6, 2008).
Snowden-Pencer, Inc., "Emory Endoplastic Instruments", Endoscopic Plastic Surgery, pp. 1-10 (1993).
Wengrovitz, "Wound Complications of Autogenous Subcutaneous Infrainguinal Arterial Bypass Surgery: Predisposing Factors and Management", vol. 11, No. 1, pp. 156-163 (Jan. 1990).
Iafrati, "Laparoscopic Cholecystectomy in the Community Hospital, our first 1.01 cases", Current Surgery, vol. 48, No. 10 (Dec. 1991).
Ashby, "Operative Choledochoscopy in Common Bile Duct Surgery", Annals of the Royal College of Surgeons of England, vol. 67, pp. 279-283 (1985).
Nezhat et al., "Salpingectomy via Laparoscopy: A new surgical approach" Journal of Laparoendoscopic Surgery (1991), http://www.ncbi.nlm.nih.gov/pubmed/1834264.
Gershman et al., "Laparoscopic Pelvic Lymphadenectomy", Journal of Laparoendoscopic Surgery, vol. 1, No. 1 (1990).

(56) References Cited

OTHER PUBLICATIONS

Leahy et al., "Minimally Invasive Esophagogastrectomy: An Approach to Esophagogastrectomy Through the Left Thorax", Journal of Laparoendosopic Surgery, vol. 1, No. 1, pp. 59-62 (Nov. 1990).
Towbin et al., "Real-Time US Guidance During Renal Biopsy in Children", Journal of Vascular and Interventional Radiology (1991), http://www.ncbi.nlm.nih.gov/pubmed/1797225.
Cooperman et al.., "Laparoscopic Colon Resection: a case report", J. Laparoendoscopic Surgery 1991, http://www.ncbi.nlm.nih.gov/pubmed/1834273.
Gunther, "Percutaneous Interventions in the Thorax", Journal of Vascular and Interventional Radiology, pp. 379-390 (May 1992).
Zuckerman et al., Splenopneumopexy: evaluation with splenoportography, Journal of Vascular and Interventional Radiology, vol. 3, No. 1 (Feb. 1992), http://www.ncbi.nlm.nih.gov/pubmed/1540718.
Tyler, "Voluntary Sterilization", American Journal of Public Health, vol. 63, No. 7, pp. 573-575 (Jul. 1973).
Yeager et al., "Surgical Management of Severe Acute Lower Extremity Ischemia", Joumal of Vascular Surgery, vol. 15, No. 2, pp. 385-393 (Feb. 1992).
Woelfle et al., "Technique and Results of Vascular Endoscopy in Arterial and Venous Reconstructions", Annals of Vascular Surgery, vol. 6, No. 4, pp. 347-356 (Jul. 1992).
Stierli et al., "Angioscopy-guided semiclosed technique for in situ bypass with a novel flushing valvulotome: Early results", Journal of Vascular Surgery, vol. 15, No. 3, pp. 564-568 (Mar. 1992).
Stahlfeld et al., "Letter to the editor: A simple technique to protect subcutaneous grafts", Journal of Vascular Surgery, p. 1080 (Jun. 1992).
Shah et al., "Is long vein bypass from groin to ankle a durable procedure? An analysis of a ten-year experience", Journal of Vascular Surgery, vol. 15 (1992).
Rosenthal et al., "Endovascular infrainguinal in situ saphenous vein bypass: a multicenter preliminary report", Journal of Vascular Surgery, vol. 16 (1992).
Pietrafitta et al., "An Experimental Technique of Laparoscopic Bowel Resection and Reanastomosis", Surgical Laparoscopy & Endoscopy, vol. 2, No. 3, pp. 205-211 (Sep. 1992).
Pier et al., "Laparoscopic Appendectomy in 625 Cases: From Innovation to Routine", Surgical Laparoscopy & Endoscopy, vol. 1, No. 1 pp. 8-13 (1991).
Pearce et al., "The Use of Angioscopy in the Saphenous Vein Bypass Graft", Technologies in Vascular Surgery, pp. 289-294 (1992).
Narayanan et al., "Experimental Endoscopic Subcutaneous Surgery", Journal of Laparoendoscopic Surgery, vol. 2, No. 3, pp. 179-183 (1992).
McPherson et al., "Intravascular Ultrasound: Principles and Techniques", Technologies in Vascular Surgery, pp. 233-241 (1992).
Jugenheimer et al., "Endoscopic Subfascial Sectioning of Incompetent Perforating Veins in Treatment of Primary Varicosis", World Journal of Surgery, vol. 16, pp. 971-975 (1992).
Harward et al., "The use of arm vein conduits during infrageniculate arterial bypass", Vascular Surgery (1992).
Flinn et al., "A comparative study of angioscopy and completion arteriography after infrainguinal bypass", Tehcnologies iin Vascular Surgery, pp. 295-305 (1992).
Dries et al., "The Influence of Harvesting Technique on Endothelial Preservation in Saphenous Veins", Journal of Surgical Research, vol. 52, No. 3, pp. 219-225 (Mar. 1992).
Taylor et al., "Technique of Reversed Vein Bypass to Distal Leg Arteries", Techniques in Arterial Surgery, pp. 109-122 (1990).
Taylor et al, "Present status of reversed vein bypass grafting: Five-year results of a modern series", Journal of Vascular Surgery, vol. 11, No. 2, pp. 193-206 (Feb. 1990).
Schmidt et al., "A Canine Model of Intimal Hyperplasia (Ih) in Autogenous Vein Grafting: A Preliminary Report", Journal of Investigative Surgery, vol. 3, No. 4, pp. 357-364 (1990).
Sadick, "Treatment of Varicose and Telagiectatic Leg Veins with Hypertonic Saline: A Comparative Study of Heparin and Saline", The Journal of Dermatologic Surgery and Oncology, vol. 16, No. 1, pp. 24-28 (Jan. 1990).
Sadick, "Sclerotherapy of Varicose and Telangiectatic Leg Veins: Minimal Sclerosant Concentration of Hypertonic Saline and Its Relationship to Vessel Diameter", The Journal of Dermatologic Surgery and Oncology, vol. 17, pp. 65-70 (1991).
Lamuraglia et al., "Angioscopy guided semiclosed technique for in situ bypass", Journal of Vascular Surgery, vol. 12, No. 5, pp. 601-604 (Nov. 1990).
Knighton et al., "Saphenous Vein in Situ Bypass", the American Journal of Surgery, vol. 160, pp. 294299 (Sep. 1990).
Feinberg et al., "The use of composite grafts in femorocrural bypasses performed for limb salvage: A review of 108 consecutive case and comparison with 57 in situ saphenous vein bypasses", Journal of Vascular Surgery (1990).
Beretta et al., "Gastroepiploic artery free graft for coronary bypass", European Journal of Cardiothoracic Surgery, vol. 4, pp. 323-328 (1990).
Troidl, "Surgical Endoscopy and Sonography", Surgical Endoscopy, vol. 4, pp. 41-46 (1990).
Cotton, "Biomedical Engineering in Vascular Surgery", Annals of the Royal College of Surgeons of England, vol. 54, pp. 22-32 (1974).
Crispin, "Arterial Endoscopy", Acta Chirurgica Belgica, No. 1, pp. 59-67 (Jan. 1974).
Plecha, "An Improved Method of Harvesting Long Saphenous Vein Grafts", Archives of Surgery, vol. 108, No. 1 (Jan.-Jun. 1974).
Vollmar et al., "Vascular Endoscopy", The Surgical Clinics of North America, vol. 54, No. 1, pp. 111-122 (Feb. 1974).
Fogarty, "Combined thrombectomy and dilation for the treatment of acute lower extremity arterial thrombosis", Journal of Vascular Surgery, vol. 10, No. 4, 530-534 (Oct. 1989).
Blanco, "Resins Aid in Bypass Surgery", Plastics Engineering (Aug. 1998).
O'Neill, "The Effects on Venous Endothelium of Alterations in Blood Flow Through the Vessels in Vein Walls, and the Possible Relation to Thrombosis", Annals of Surgery, vol. 126, No. 3, pp. 270-288 (Sep. 1947).
Matsumoto et al., "Direct Vision Valvulotomy for Nonreversed Vein Graft", Sugery Gynecology & Obstetrics, vol. 165, No. 2, pp. 180-182 (1987).
Hauer, "Surgery of Perforating Veins", Langenbecks Archive Chirurgie Supplement, pp. 464-465 (1992).
Pierik et al., "Subfascial Endoscopic Ligation in the Treatment of Incompetent Perforating Veins", European Journal Vascular Endovascular Surgery, vol. 9, pp. 38-41 (1995).
Gottlob, "Reconstruction of Venous Valves", Venous Valves: Morphology Function Radiology Surgery, pp. 188-213(1986).
Berci, "Techiques for improving illumination and recording in endoscopy", Optics and Laser Technology, pp. 31-37 (Feb. 1976).
Berci, Endoscopy today and tomorrow (1976).
Shumacker, "Weglowski's Pioneering Vascular Surgery and Barriers to Progress", Current Critical Problems in Vascular Surgery, vol. 3 (1991).
Buchbinder et al., "B-mode Ultrasonic Imaging in the Preoperative Evaluation of Saphenous Vein", The Ainerican Journal, vol. 53, No. 7, pp. 368-372 (Jul. 1987).
Hoffmann, "Die subfasziale, endosopische Laser—Perforantes-Dissektion unter Berucksichtigung auch der lateralen Perforansvenen", Vasomed, vol. 9, No. 5 (1997).
Fischer, "Eine neue Generation der Varizenchirurgie", VASA, Band 20, pp. 311-318 (1991).
Jugenheimer et. al., "Ergebnisse der endoskopischen Perforans-Dissektion", Der Chirurg, pp. 625-628 (Aug. 1991).
Kern et al, "Technique of coronary angioscopy" (2008), http://www.uptodate.com/patients/content/topic.do.
Frazee, "Neuroendoscopy Program" (2008), http://neurosurgery.ucla.edu/body.cfm.
"Preceptor", http://dictionary.reference.com/browse/preceptor.
Berci et al., "History of Endoscopy", Surgical Endoscopy, vol. 14, pp. 5-15 (2000).

(56) References Cited

OTHER PUBLICATIONS

"Ultrasound and Interventional Techniques", Surgical Endoscopy, vol. 10, No. 1 (Jan. 1996).
"Minimal Invasive Surgery", Surgical Endoscopy: Ultrasound and Interventional Techniques, vol. 10, No. 1 (Jan. 1996).
"The Eyes of the Wolf are Sharper", Surgical Endoscopy: Ultrasound and Interventional Techniques, vol. 10, No. 3 (Mar. 1996).
"Endoscopic suturing made easy", Surgical Endoscopy: Ultrasound and Interventional Techniques, vol. 9, No. 2 (Feb. 1995).
"Instruments for percutaneous nucleotomy and discoscopy", Surgical Endoscopy: Ultrasound and Interventional Techniques, vol. 3, No. 1 (1995).
"Fiberscope for vascular endoscopy", Surgical Endoscopy: Ultrasound and Interventional Techniques, vol. 3, No. 2 (1989).
"Narrow operative approach, atraumatic examination. The Karl Storz Neuro-Endoscope", Surgical Endoscopy vol. 3, No. 3 (1989).
"Fiberscope for vascular endoscopy", Surgical Endoscopy vol. 3, No. 4 (1989).
"New: Universal-Neuro-Endoscope. New application possibilities for Neurosurgery", Surgical Endoscopy vol. 4, No. 1 (1990).
Springer book advertisement, Surgical Endoscopy vol. 4, No. 4 (1990).
Richard Wolf advertisement, Surgical Endoscopy, vol. 5, No. 1 (1991).
"Why do open surgery", Surgical Endoscopy, vol. 5, No. 2 (1991).
"Minimally invasive surgery. Operating proctoscope for anal surgery", Surgical Endoscopy, vol. 5, No. 3 (1991).
"Laparoscopic Surgery . . . The Next Generation", Surgical Endoscopy, vol. 6, No. 2 (1992).
"There's a Revolution in Surgery. USSC was there in the beginning", Surgical Endoscopy, vol. 6, No. 3 (1992).
"Cuschieri Thoracoscopic Instruments", Surgical Endoscopy, vol. 6, No. 4 (1992).
"Laparoscopic has just turned a new corner . . . ", Surgical Endoscopy, vol. 6, No. 5 (1992).
"Electronic Video Laparoscopy", Surgical Endoscopy, vol. 6, No. 6 (1992).
"Performing a Nissen just got easier, faster, and cheaper", Surgical Endoscopy, vol. 9, No. 9 (1995).
"Easy entry . . . maximizes safety . . . ", Surgical Endoscopy, vol. 9, No. 5 (1995).
"Richard-Allan Medical Has Just Bent the Rules on Endoscopic Cutting", Surgical Endoscopy, vol. 10, No. 9 (1996).
"High quality endoscopic instruments", Surgical Endoscopy, vol. 10, No. 11 (1996).
"Endoscopic Surgery of the Paranasal Sinuses and Anterior Skull Base", Endoscopy, vol. 22, No. 5 (1990).
"Karl Storz—Endoscopes for bronchoscopy", Endoscopy, vol. 23, No. 1 (1991).
"Original Karl-Storz. System Perfection", Endoscopy, vol. 23, No. 3 (1991).
"Minimally invasive surgery.Laparascopic cholecystectomy", Endoscopy, vol. 23, No. 4 (1991).
"Greater Visibility, Lighter Weight ", Endoscopy, Vo. 23, No. 5 (1991).
"A Different View on Diagnosis: (Toshiba Medical Systems) and 2 Live International Therapeutic Endoscopy Course in Mexico City Oct. 10-12, 1990", Endoscopy, vol. 22, No. 3 (1990).
ProMIS Line: The complete endoscopy program from AESCULAP, Endoscopy, vol. 28, No. 3 (1996).
"Now you can afford to change your point of view", Endoscopy, vol. 27, No. 3 (1995).
"Karl Storz endoscopes for NEODYM—YAG and CO2 lasers", E 1990, Endoscopy, vol. 22, No. 1 (1990).
"Endoscopic Ultrasonography: EUS", Endoscopy, vol. 22, No. 2 (1990).
"A new sense of security in endoscopic ligation", Sugical Laparoscopy & Endoscopy.
"Laparoscopic Surgery . . . The Next Generation." Surgical Laparoscopy & Endoscopy.

"The Olympus Laparoscopic Cholecystectomy System: Resolution for Gallstones with the Leader in Higher Resolution Optics", Surgical Laparoscopy & Endoscopy.
"Cabot Laparoscopic Irrigation System: Dissect/Lase/Cut/Irrigate/Aspirate through a single puncture", Surgical Laparoscopy & Endoscopy.
"Laparoscopic Cholecystectomy: a Minimally Invasive Treatment for Gallbladder Disease", Surgical Laparoscopy & Endoscopy.
"The DaVinci Line", Surgical Laparoscopy & Endoscopy.
Surgical Laparoscopy & Endoscopy, vol. 1 No. 1 (1991).
Surgical Laparoscopy & Endoscopy, vol. 1, No. 2 (1991).
Surgical Laparoscopy & Endoscopy, vol. 1, No. 3 (1991).
Surgical Laparoscopy & Endoscopy, vol. 1, No. 4 (1991).
Surgical Laparoscopy & Endoscopy, vol. 2, No. 1 (1992).
Surgical Laparoscopy & Endoscopy, vol. 2, No. 2 (1992).
Surgical Laparoscopy & Endoscopy, vol. 2, No. 3 (1992).
Surgical Laparoscopy & Endoscopy, vol. 2, No. 4 (1992).
"Karl Storz Take-apart: The fully cleanable cost-effective, modular instrument solution", Surgical Laparoscopy & Endoscopy, vol. 6, No. 1 (1996).
Cuschieri, "How I Do It", Laparoscopic cholecystectomy (Mar. 1999).
"History of Endoscopy" (2008), http://wwww.alexea.org/.
"Laparoscopy" (1998), http://www.ehealthmd.corn/library/laparoscopy/LAP—whatis.html.
White et al., Coronary Angioscopy, vol. 22, No. 1, pp. 20-25 (1995).
"If you need a better grasp of endoscopy, Weck;s new Hasson Graspers will let you do more than pinch an inch".
Advertisement: Cooper Endoscopy.
"Control at Your Finger Tips: For Advanced Laparoscopic Surgery", Mectra Labs, Inc.
Nanticoke Advanced Laparoscopic/Thoracoscopic Instruments for the next generation of endoscopic surgery°, Cabot Medical.
Minimally Invasive Surgery: Laparoscopic Cholecystectomy°, Karl Storz Endoscopy.
Advertisement: "Our New Line of Weck Instruments Brings the Feel of Open Surgery to Endoscopy", Linvatect Weck Endoscopy.
"Let Olympus Take You Where you Want to Go", Olympus Corporation.
"Beyond Laparoscopic Cholecystectomy: A Hands-On Course".
"The Surgical Expertise Remains in your Hands . . . Now Trust Olympus to be Your Eyes . . . ", Olympus Corporation.
"Special Needs. Special Designs.", Snowden-Pencer.
"The DaVinci Line", DaVinci Medical.
"The Standard for Laparoscopic Surgery", American Surgical Instruments, Inc.
"VirtuoSaph Endoscopic Vein Harvesting System MCVS550", Terumo (product description).
Olympus Endoscopic Accessories Price List, Effective Feb. 15, 1986.
Feldman, "Laparoscopic Nephrectomy", The New England Journal of Medicine, vol. 325, No. 15, pp. 1110-1111 (Oct. 10, 1991).
History of Endoscopy, http://laparoscopy.blogs.com/endoscopyhistory/table—of —contents/.
Kunlin, "Le traitement de fischamie arteritique pas la greffe veineuse longue", Revue de Chirurgie, pp. 206-235 (Aug. 1951).
Stanley et al. Autogenous Saphenous Vein as an Arterial Graft:Clinical Status in Stanley JC (ed): Biologic and Synthetic Vascular Prostheses, New York, Gmne and Stratton, Inc. 333-349 (1982).
Cohen et al Indications for Left Ventricular Aneurysmectomy Circulation 1983; 67; 717-722.
Evdokimov et al., "A Combination of Electroacupuncture and Conduction Anesthesia in Operations for Varicose Dilatation of Lower Extremity Veins", ISSN 0042-4625 (1985).
Lofgren Treatment of Long Saphenous Varicosities and Their Recurrence:A Long-Term Follow-Up, Surgery of the Veins, Grune & Stratton (1985).
Meldrum-Hanna et al. An Improved Technique for Long Saphenous Vein Harvesting for Coronary Revascularization, Annals of Thoracic Surgery 1986 42: 90-92.
Gottlob et al. Replacement of Small Veins by Autologous Grafts: Application of an Endothelium-Preserving Technique, Vasc Endovascular Surg. 1982; 16; 27 Vienna and New York.
Lukomskii, "Prevention of Post" (1986).

(56) References Cited

OTHER PUBLICATIONS

Nagovitsyn, "Endoscopic Coagulation of the Communicating Veins of the Leg in Chronic Venous Insufficiency", Sovetskaia Meditsina, vol. 12, pp. 109-110 (1987).
Buchbinder et al. B-Mode Ultrasonic Imaging in the Preoperative Evaluation of Saphenous Vein, American Surgeon, 1987 Jul., vol. 53, No. 7.
Sottiurari et al. Autogenous Vein Grafts:Experimental Studies, in Stanley JC (ed): Biologic and Synthetic Vascular Prostheses, New York, Gmne and Stratton, Inc. 311-331 (1982).
Hauer, "Operationstechnik der Endoskopischen Subjascialen Discision der Perforansvenen", Chirurg, vol. 58, pp. 172-175 (1987).
Nagovitsyn, "Endoscopic Electrocoagulation of the Communicating Crural Veins", Khirurgiia (Mosk), vol. 12, pp. 60-61 (Dec. 1987).
Devambez et al., "Ecarteur Autostatique Pour Chirurgie de Varices", Phlebologie: Bulletin de la Societe Francaise de Phlegologie (1988).
Nagovitsyn, "Vein-sparing operations combined with endoscopic electrocoagulation of the communicating veins", Vestnik Khirurgii, vol. 140, No. 3, pp. 92-93 (Mar. 1988).
Nagovitsyn, "Prevention of complications for endoscopic correction of the crural venous blood flow", Vestnik Khirurgii, vol. 142, No. 3, pp. 113-115 (Mar. 1989).
Bailey et al., "Laparoscopic Cholecystectomy: Experience with 375 Consecutive Patients", Ann. Surg. (Oct. 1991).
Maignien, "Splenectomie par vote ccelioscopique 1 observation", La Presse Medicate (Dec. 21-28, 1991).
Moll, "Historische Anmerkungen zur Entwicklung von Endoskopie and minimal invasiver Operations-technik", Geschichte der Medizin (1993).
Markstrom, "Intraoperativ angioskopi via infrainguinal bypass med vena saphena magna in situ", Medicinsk Rapport, vol. 89, No. 49 (1992).
Fischer, "Die chirurgishe Behandlung der Varizen Grundlagen and heutiger Stand: Surgery of Varicose Veins", Scheweiz. Rundshau Med. (Praxis), vol. 79. No. 7 (1990).
Devambez et al., "Self-Retaining retractor for surgery of varices", Phlebologie, vol. 41, No. 2, pp. 297-299 (1988).
Endoscopy vol. 22, No. 4, 1990]: Document in German language 1990.
Vandamme, Jean-Pierre and Bonte, Jan, Vascular Anatomy in Abdominal Surgery, Thieme MediCal Publishers, Inc. New York (1990).
Swobodnik, Atlas of Ultrasound Anatomy, Thieme Medical Publishers, Inc., New York (1991).
Curriculum Vitae of Albert K. Chin, M.D.
Respondent Terumo Cardiovascular Systems Corporation's Supplemental Responses to Maquet Cardiovascular L.L.C.'s Interrogatory Nos. 29, 32-33, 45-46, 51-62, 64 and 78 [redacted version with attached claim charts] Aug. 15, 2008.
Terumo's Proposed Claim Construction Oct. 31, 2008.
Maquet's Proposed Claim Constructions Oct. 31, 2008.
Maquet's Proposed Claim Constructions with Supporting Authority Nov. 19, 2008.
Order Granting/Denying Request for Reexamination from 90/004,301 Patent Application.
Public Complaint of Maquet Cardiovascular L.L.C. Under Section 337 of the Tariff Act of 1930 as Amended w/all exhibits Apr. 1, 2008.
Public Response of Respondents Terumo Corporation and Terumo Cardiovascular Systems Corporation to the Complaint and Notice of Investigation Jun. 9, 2008.
Public Amended Response of Respondents Terumo Corporation and Terumo Cardiovascular Systems Corporation to the Complaint and Notice of Investigation Oct. 27, 2008.
Respondent Terumo Cardiovascular Systems Corporation's Responses to Maquet Cardiovascular LLC's Seventh Set of Interrogatories (Nos. 91-95) Aug. 15, 2008.
Respondent Terumo Cardiovascular Systems Corporation's I Responses to Maquet Cardiovascular LLC's Third Set of Interrogatories [No. 78] Jun. 30, 2008.
Respondent Terumo Corporation's Responses to Maquet Cardiovascular LLC's Third Set of Interrogatories (No. 78) Jun. 30, 2008.
Respondent Terumo Corporation's Responses to Maquet Cardiovascular LLC's Sixth Set of Interrogatories (Nos. 82-86) Aug. 15, 2008.
File History of U.S. Patent No. Re 36,043.
File History of U.S. Appl. No. 10/897,157.
File History of U.S. Appl. No. 10/052,016.
File History of U.S. Patent No. 7,326,178.
File History of U.S. Patent No. 5,993,384.
File History of U.S. Patent No. 5,895,353.
"Current critical problems in vascular surgery" vol. 3, Ch 11-18, 25, 26, 29-31, 33-36, 45-49, 65, ISBN 0-942219-24-4.
Berci, "Endoscopy", 1976, ISBN 0/8385-2216-5.
"Enter a new realm", 2007, by Boston Scientific Corp.
"Vasoview competitive advantage", 2007, by Boston Scientific Corp.
"VasoView HemoPro endoscopic vessel harvesting system", 2007, by Guidant.
Decision to merge reexamination and reissue proceedings for U.S. Patent No. 5,373,840 (control No. 90/004,301).
U.S. Appl. No. 60/148,130, filed Aug. 10, 1999, Chin.
U.S. Appl. No. 60/148,130, filed Aug. 25, 1999, Chin.
U.S. Appl. No. 08/269,666, filed Jul. 1, 1994, Chin.
U.S. Appl. No. 08/502,494, filed Mar. 14, 2004, Chin et al.
U.S. Appl. No. 08/593,533, filed Jan. 24, 1996, Chin.
U.S. Appl. No. 09/133,136, filed Aug. 12, 1998, Chin.
U.S. Appl. No. 09/227,393, filed Jan. 8, 1999, Lunsford et al.
U.S. Appl. No. 09/413,012, filed Oct. 5, 1999, Chin et al.
U.S. Appl. No. 09/635,721, filed Aug. 9, 2000, Chin.
U.S. Appl. No. 09/738,608, filed Dec. 14, 2000, Chin.
U.S. Appl. No. 09/739,595, filed Dec. 15, 2000, Chang.
U.S. Appl. No. 09/750,848, filed Dec. 27, 2000, Chin.
U.S. Appl. No. 10/345,666, filed Jan. 16, 2003, Stack.
U.S. Appl. No. 10/371,537, filed Feb. 21, 2003, Beavers.
U.S. Appl. No. 11/962,517, filed Dec. 21, 2007, Chin.
U.S. Appl. No. 90/004/4.301, filed Jul. 12, 1996, Knighton et al.

* cited by examiner

SECTION A-A

SECTION B-B

TISSUE DISSECTOR APPARATUS AND METHOD

RELATED APPLICATION DATA

This application is a continuation of U.S. patent application Ser. No. 13/092,826 filed on Apr. 22, 2011, now U.S. Pat. No. 8,460,331; which is a continuation of U.S. patent application Ser. No. 09/413,012, filed on Oct. 5, 1999, now U.S. Pat. No. 7,938,842; which is a continuation of U.S. patent application Ser. No. 09/133,136, filed on Aug. 12, 1998, the entire disclosures of all of which are expressly incorporated by reference herein.

FIELD OF THE INVENTION

The present invention relates to the field of surgical apparatus, and more particularly to endoscopic vessel isolators.

BACKGROUND OF THE INVENTION

During surgical harvesting of vessels, a target vessel is exposed, tributaries are ligated and transected, and the vessel is harvested. In order to view the vessel, a cannula housing an endoscope is inserted into a surgical cavity to visualize the adventitial layer of a target vessel. The vessel is tracked by advancing the cannula along the path of the vessel while bluntly dissecting the cavity as the cannula is advanced. Upon viewing a side branch or tributary of the vessel, a surgical tool is inserted into the surgical cavity to cauterize and sever the side branch. The endoscope remains in the surgical cavity during this process to allow the surgeon to view the procedure, and the size of the cavity is maintained using insufflating gas. Using different tools simultaneously in a surgical cavity is difficult due to the small size of the surgical cavity. Additionally, within the surgical cavity, the surrounding tissue typically collapses upon the cannula and surgical tools, increasing the difficulty of the operation, if performed without insufflation. However, maintaining the surgical cavity open using insufflation with gas under pressure then also requires sliding gas-tight seals for each endoscopic instrument that is inserted into the surgical cavity.

Current systems commonly employ a balloon coupled to the cannula for intermittent inflation and deflation to enlarge the surgical cavity as the cannula is advanced. However, use of a balloon to enlarge surgical cavities has the disadvantage that multiple balloon inflation and deflation tires the surgeon's hands, and makes it difficult to retain the precise hand control needed to perform the surgical procedure. Also, manufacture of a balloon cannula requires manual mounting of the balloon in a tedious process that adds expense to the device. Additionally, balloons have a potential for rupture during use and thereby disrupt the surgical procedure. Thus, a device is needed which retains the endoscopic vessel tracking ability of current systems, while also enlarging the surgical cavity without the disadvantages of balloon systems.

SUMMARY OF THE INVENTION

In accordance with the present invention, a tissue dissector is provided in which a cannula houses an endoscope, and a dilating element is coupled near the distal end of the cannula. The dilating element has an outer dimension which is greater than the diameter of the distal end of the cannula. This greater dimension serves to enlarge the surgical cavity as the cannula is advanced through the surgical site, thus allowing the cannula to track along the vessel while forming a working cavity and providing room within which additional surgical tools may operate safely. In one embodiment, the dilating element is in the shape of an oval, allowing compression of the surrounding tissue to occur atraumatically.

In an alternate embodiment, a locking mechanism is disposed on the cannula, and the dilating element is coupled to the locking mechanism when enlargement of the surgical cavity is required. In this embodiment, multiple dilating elements of differing outer dimensions may be employed responsive to the enlargement required. Various locking mechanisms may be employed in accordance with the current invention, including using screw threads disposed on the surface of the cannula, and mating internal screw threads in a bore hole through the dilating element to permit the dilating element to couple to the screw threads. Alternatively, the dilating element may include a bayonet-type fitting, with mating knobs on the associated surface portion of the cannula for locking the dilating element into place. Additionally, in one embodiment the tip and dilating element are a single detachable component, and may be coupled and decoupled to the main body of the cannula as desired. This greatly facilitates use of dilating elements of different dimensions.

The body of the cannula may be tapered from a smaller diameter near the distal end of the cannula to a larger diameter remote from the distal end of the cannula. The tip of the cannula is transparent to facilitate endoscopic viewing of the surgical cavity. The tapering of the distal end of the cannula may begin at a point forward of the distal end of the dilating element. This allows the tip of the cannula to track along the target vessel without the enlarged diameter of the dilating element preventing the tip from making contact with the target vessel. In one embodiment, the dilating element is made of rigid plastic to facilitate expansion of a working cavity and ease of translation through the surgical site. In another embodiment, the dilating element is made of a flexible material which compresses as the external walls exert force upon the cannula but retains sufficient structural rigidity to accomplish the required enlargement of a working cavity. In yet another embodiment, the dilating element is made of flexible material and is shrouded within a retractable sheath which, in the extended position, encases the dilating element and thereby compresses the dilating element to a smaller diameter, and in a retracted position, allows the dilating element to expand and enlarge the working cavity.

Methods are also disclosed for dissecting an elongated cavity along the course of a vessel using a cannula according to one or other embodiments of the present invention, including incising the skin of a patient, placing the tip of the cannula along the surface of the vessel, advancing the cannula along the vessel under continuous endoscopic visualization through the tip, enlarging the cavity about the outer dimension of the dilating element, removing the cannula upon reaching the desired length of the target vessel, and optionally placing a sealing trocar in the incision and maintaining the enlargement by insufflating the subcutaneous tunnel with gas under pressure. The vessel may then be harvested through a separate incision near the remote end of the surgical cavity.

BRIEF DESCRIPTION OF THE DRAWINGS

FIG. 5b is a side view of a dilating element for locking attachment to the cannula in FIG. 5a.

FIG. 5c is a cut-away side sectional view of the dilating element for use with the cannula of FIG. 5a.

FIG. 6b is a side view of a dilating element for locking attachment to the cannula of FIG. 6a.

FIG. 6c is a cut-away side sectional view of the dilating element for use with the cannula of FIG. 6a.

DETAILED DESCRIPTION OF THE INVENTION

Figure 1:
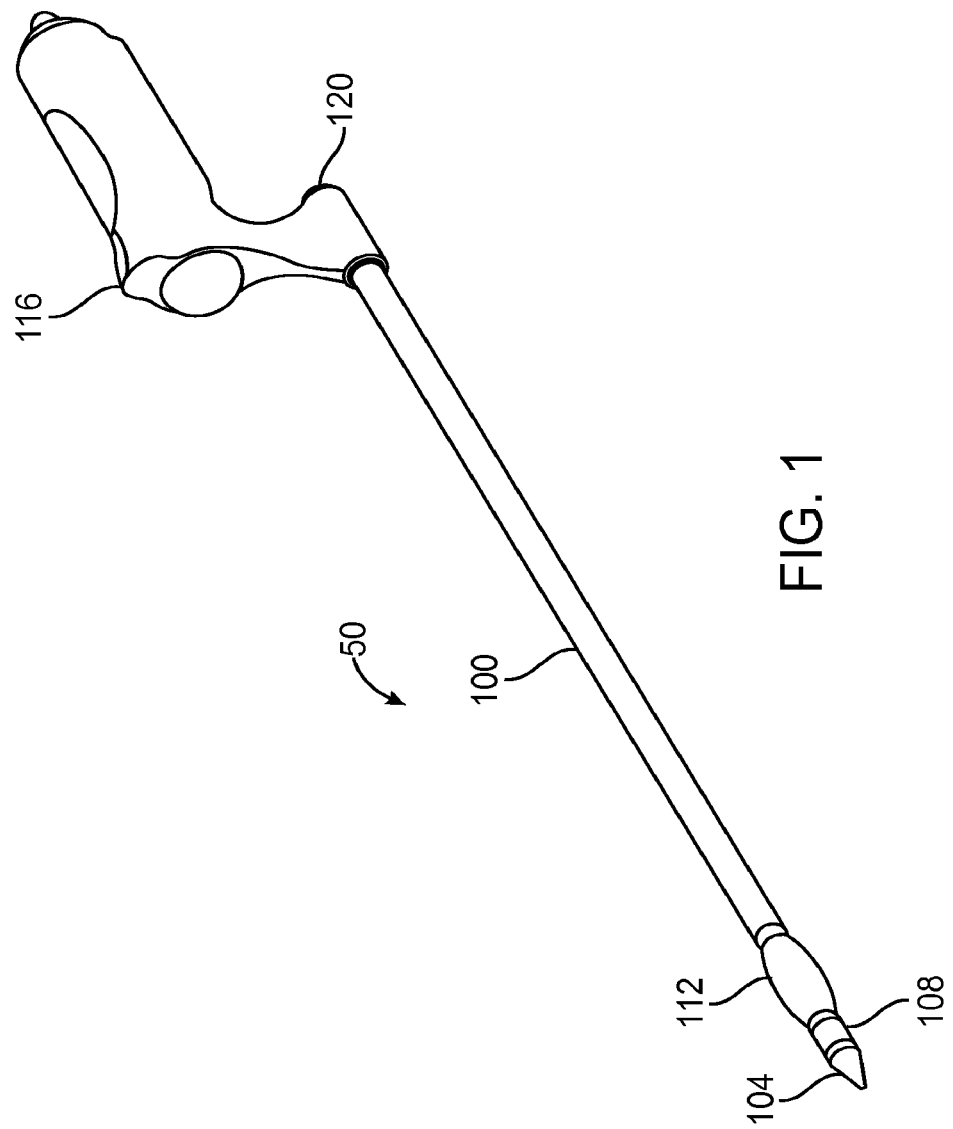
FIG. 1 illustrates a perspective view of the cannula in accordance with one embodiment of the present invention.

FIG. 1 illustrates a tissue dissector 50 in which a cannula 100 is coupled to a dilating element 112. The proximal end of cannula 100 is coupled to a handle 116 and the distal end of cannula 100 is enclosed by transparent tapered tip 104. Dilating element 112 is positioned inwardly from the distal end of the cannula 100. Cannula 100 may be made from a variety or combination of bioinert, substantially inelastic materials, such as stainless steel, polyethylene, polyurethane, polyvinyl chloride, polyimide plastic and the like that preferably have a tensile strength of at least 10,000 psi. Handle 116 is ergonomically formed to allow a surgeon to easily and comfortably manipulate cannula 100 within a surgical cavity.

Figure 2:
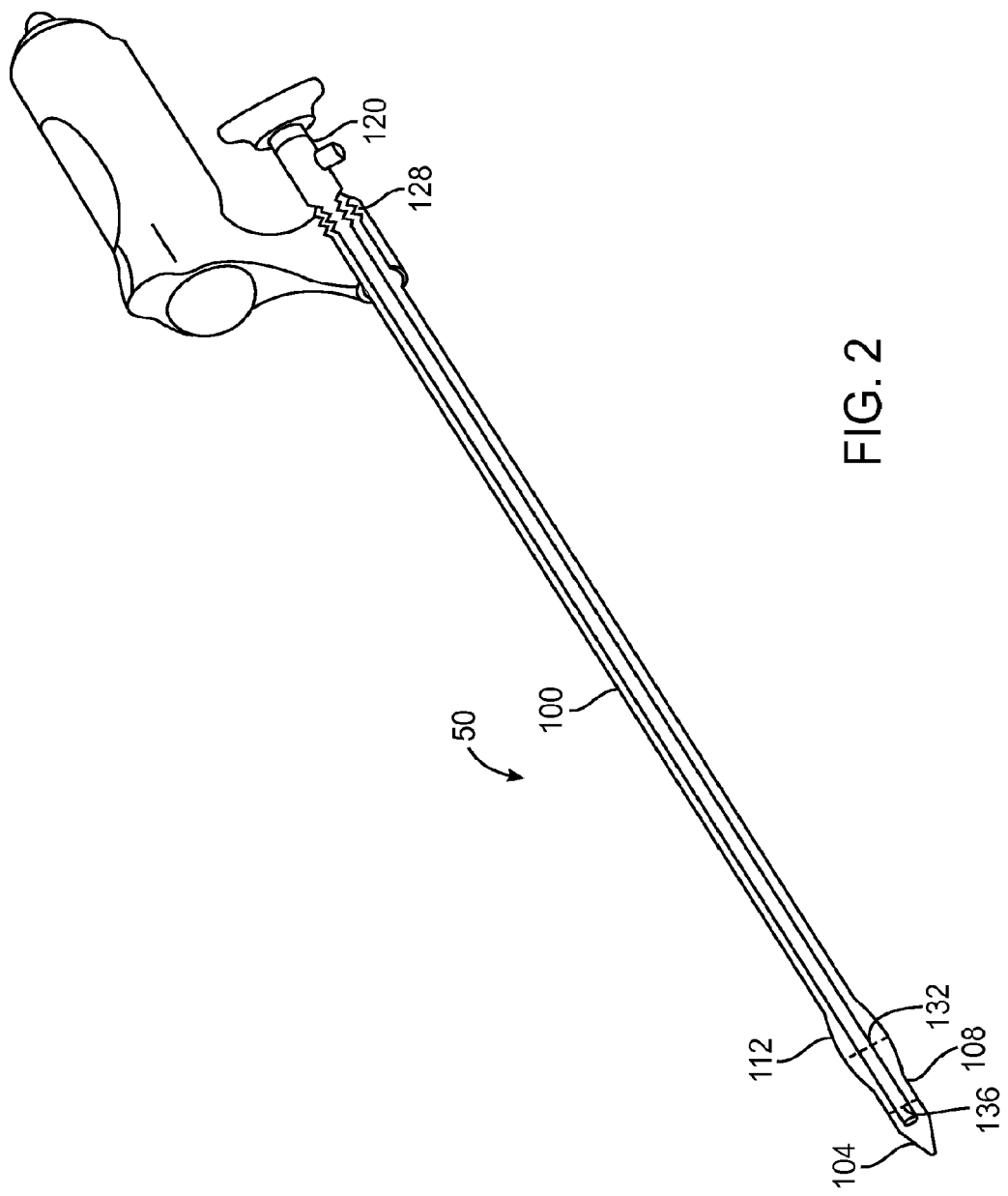
FIG. 2 is a cut-away side sectional view of the cannula in accordance with the present invention.

FIG. 2 illustrates a cut-away side sectional view of tissue detector 50. As shown, the distal end of cannula 100 has an outer diameter or dimension 136, and the dilating element 112 has an outer dimension 132 which is greater than the diameter 136. The proximal portion of cannula 100 preferably has a smaller dimension than the dilating element 112 to allow more flexibility in maneuvering the cannula 100 in the surgical site. The greater dimension 132 of dilating element 112 enlarges or expands a surgical cavity by pushing away surrounding tissue within a surgical cavity as the cannula 100 is advanced through a surgical site. The surgical cavity may thus be formed adjacent to a target vessel as a result of the blunt tissue dissection caused by the tapered tip 104 as it is advanced along the path of a target vessel, such as the saphenous vein. A preferable diameter 136 of cannula 100 is about 8.5 mm and preferable outer dimensions 132 of dilating elements 112 are in the range from about 15 mm to about 30 mm. Thus, in application, a surgical cavity is initially formed by the tapered tip 104, and is initially increased or enlarged to the diameter 136 of the distal end of cannula 100. Additionally, in accordance with the present invention, the surgical cavity is further enlarged by the dilating element 112 substantially to the dimension 132 of the dilating element 112 and this latter enlargement or expansion of a surgical cavity constitutes two or three times greater enlargement than the enlargement of such a surgical cavity by the diameter 136 of the distal end of the cannula 100. This enhanced enlargement of a surgical cavity eases further dissection of tissue as the cannula 100 is advanced along a target vessel, and facilitates subsequent manipulation of surgical tools within such surgical cavity.

Cannula 100 houses an endoscope 120 for viewing the surgical site and the target vessel through the transparent tip 104. The proximal end of endoscope 120 is attached to the proximal end of the cannula 100 by mating screw threads 128 at the proximal end of the cannula 100 and the proximal end of the endoscope 120 for fixedly positioning the endoscope 120 within the cannula 100. The proximal end of the endoscope 120 may include an eyepiece or camera attachment, or the like (not shown), and the distal end of the endoscope 120 is positioned near the distal end of the cannula 100 in alignment with the tip 104 for visualization there through of tissue being bluntly dissected thereby as the cannula 100 is advanced along a target vessel.

Figure 3:
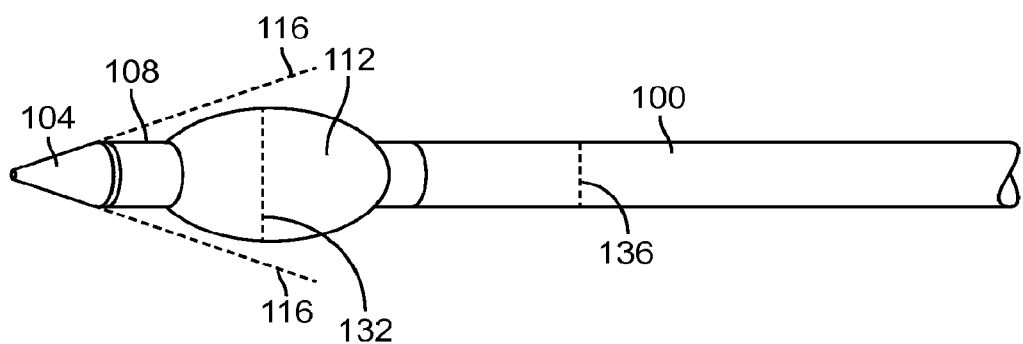
FIG. 3 is a perspective view of the distal end of cannula in accordance with the present invention.

Referring to FIG. 3, tip 104 is made of a transparent material, such as polycarbonate plastic. Positioning endoscope 120 near the distal end of cannula 100 and in alignment with the transparent tip 104 therefore allows a surgeon to view objects forward of the cannula 100. This enables the surgeon to advance the cannula 100 along the path of a target vessel, and to view and thereby avoid avulsing any side branches. Tip 104 is tapered from the distal end thereof (that is blunted with a radius of about 0.045 inches) to the larger diameter of the proximal end of tip 104 that is approximately the diameter 136 of the distal end of the cannula 100. Tapering of the tip 104 over a taper length of about 0.500 to about 0.800 inches allows advancement of the cannula along the vessel without excessive force and injury to the vessel, as well as better visualization via the endoscope 120 of a target vessel through the tapered walls of the transparent tip 104.

In order to track the path of a target vessel effectively, the tapered wall of tip 104 is placed against the target vessel as the cannula 100 is advanced through connective tissue. The taper angle 116 of the tip 104 allows the target vessel to be seen more clearly and allows a length of vessel equivalent to the length of the taper of the tip 104 to be seen by the surgeon. In order to enable the tapered wall of tip 104 to lay against the target vessel, a spacer length 108 of cannula 100 between the dilating element 112 and the proximal end of tip 104 is provided to set the dilating element 112 back behind the taper angle 116 of the tapered wall of tip 104. This spacer length 108 of cannula 100 may have a diameter substantially equal to the outer diameter 136 of the distal end of the cannula 100. The spacer length prevents dilating element 112 from interfering with the contacting of the target vessel by the walls of the tapered tip 104, at taper angle 116. Without an intervening spacer length 108, the dilating element 112 more closely adjacent the tip 104 would prevent the tapered wall of tip 104 from contacting the target vessel within the taper angle 116, and this would increase the force exerted on the target vessel during cannula advancement. In one embodiment, the distal end of dilating element 112 is 14-28 mm from the proximal end of the tip 104. Cannula 100 is preferably about 32-47 cm long and tip 104 is preferably about 10-15 mm long.

Dilating element 112 is preferably formed of Teflon or polyurethane, or polycarbonate, or the like, to form a rigid shape which compresses or otherwise displaces tissue on the walls of the surgical cavity to form an enlarged surgical cavity. In an alternate embodiment, dilating element 112 comprises resilient foam which compresses in response to an applied external force. For example, pressure from inserting the dilating element 112 into a small incision may reduce the diameter of the dilating element 112 and prevent the dilating element 112 from causing further rupture or tearing of the incision. Since the tissue typically surrounding a target vessel such as the saphenous vein is soft fatty tissue, a foam dilating element 112 with sufficient resilience and rigidity may push back the fatty tissue and enlarge a surgical cavity adjacent the vessel. Dilating element 112 is preferably of oval shape to facilitate atraumatic expansion of the surrounding tissue following blunt dissection of the fatty tissue by the tapered tip 104. Of course, other shapes of dilating element 112 may be used that have maximum dimensions 132 greater than the dimension of the proximal end of tip 104.

Figure 4:
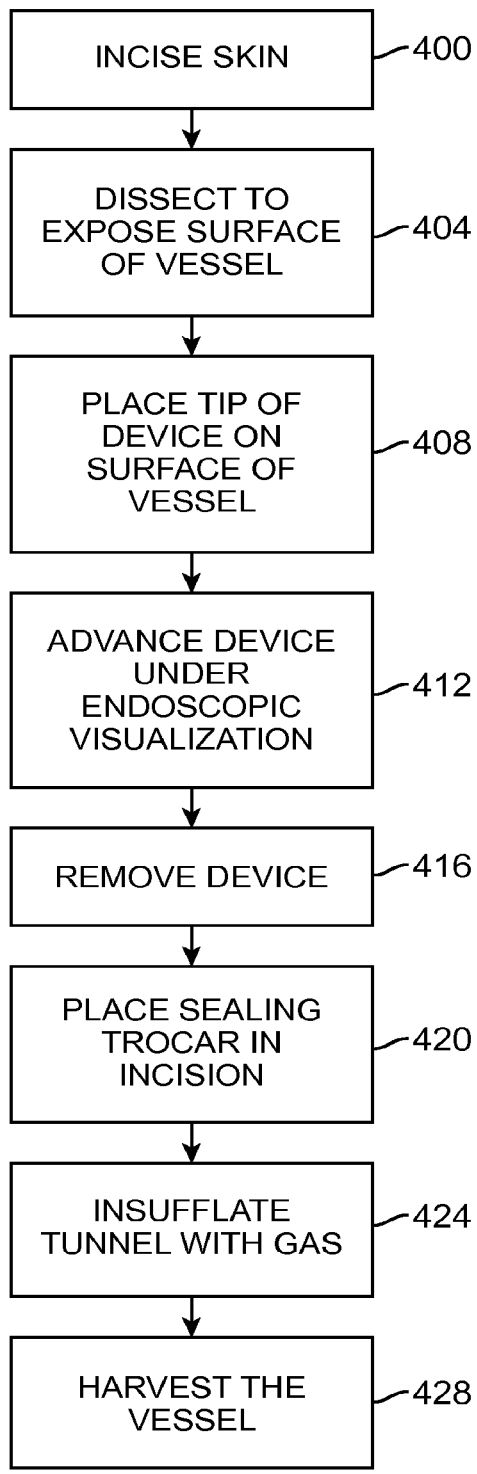
FIG. 4 is a flow chart illustrating the application of cannula in accordance with the present invention.

In application, as shown in FIG. 4, the surgeon incises 400 the skin of the patient and dissects 404 to expose the surface of the target vessel. The surgeon next places 408 the tapered wall of the transparent tip 104 on the surface of the vessel and advances 412 the tip 104 and cannula 100 under endoscopic visualization through the tip 104 along the path of the target vessel. Following dissection of the cavity along the vessel, the cannula 100 is removed 416, and a sealing trocar may be placed 420 in the incision for insufflating 424 the subcutaneous tunnel with gas under pressure to maintain the enlargement of the cavity. The vessel thus isolated is then harvested 428. A combined endoscopic and dissection instrument may be introduced through the sealing trocar to ligate and remove the target vessel for use, for example, as a coronary artery or peripheral vascular bypass graft. Alternatively, the isolated vessel may be left in place for surgical formation of an in-situ femoropopliteal or femoral-distal graft. Alternatively, following incision of the skin of the patient and dissection to expose the surface of the target vessel, gas insufflation may be initiated through a sealing trocar. The sealing trocar may be loaded onto the shaft of the cannula 100 prior to fixation of the dilating element 112 (if the outer dimension 132 of the dilating element 112 is greater than the inner diameter of the sealing trocar). The advancement 412 of the cannula 100 may then be conducted under gas insufflation, to improve visualization of the previously formed surgical cavity.

Figure 5A:
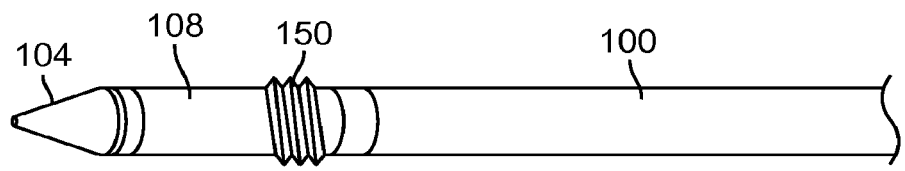
FIG. 5a illustrates a cannula having a locking mechanism in accordance with one embodiment of the present invention.
Figure 5B:
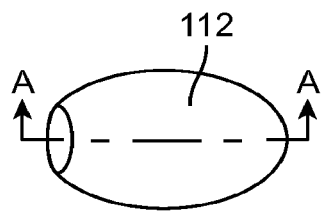

FIG. 5a illustrates an embodiment of cannula 100 with a locking mechanism 150 for a detachable dilating element 112 as shown in FIG. 5b. Locking mechanism 150 includes a length of screw threads disposed on the surface or outer housing of the cannula 100 at a position near the distal end of the cannula that allows the locked dilating element 112 to be located in a position on the cannula 100 as described previously herein with reference to FIGS. 1-3.

Figure 5C:
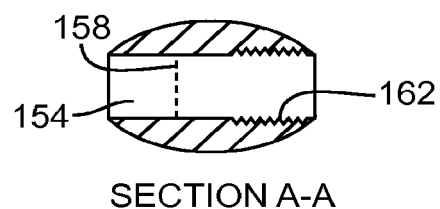

FIG. 5c illustrates a cross-section of the dilating element 112 having a mating lock or set of screw threads 162 which couples to locking mechanism 150 of FIG. 5a. A bore hole 154 is formed along the horizontal axis of the dilating element 112 and the screw threads are disposed along a portion of the bore hole 154 as a mating lock 162. The dimension 158 of the bore hole 154 is wider than the diameter 136 of the cannula 100 but is small enough to ensure a tight coupling upon inserting the dilating element 112 into the locking mechanism 150. Thus, in this configuration, the dilating element 112 is locked onto the cannula 100 by rotating the grooved end of the dilating element 112 around the shaft of the cannula 100 until the distal end of the screw threads 150 on the cannula 100 contacts the unthreaded portion of the dilating element 112 in the bore hole 154. At this point, the dilating element 112 is locked.

Figure 6A:
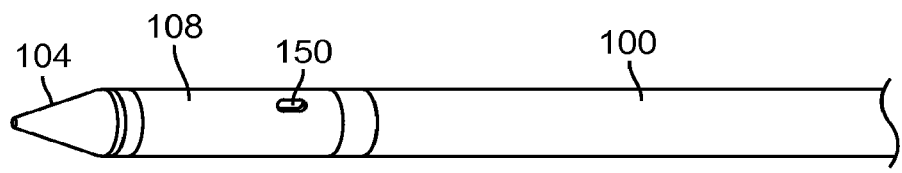
FIG. 6a is a cannula having an alternate embodiment of a locking mechanism in accordance with the present invention.
Figure 6B:
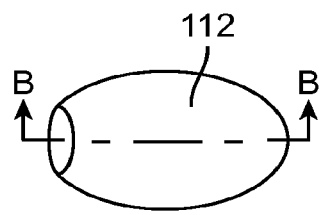
Figure 6C:
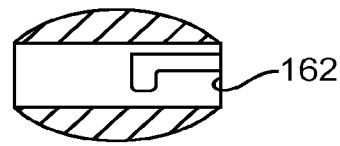

FIG. 6a illustrates an alternate embodiment of locking mechanism 150. A knob or protuberance is disposed on the surface of cannula 100 for mating with a corresponding groove 162, as shown in FIG. 6c, in the dilating element 112. The groove 162 is formed to slide over knob 150 and mate therewith through partial rotation on the cannula 100 for locking the dilating element 112 of FIG. 6b in place. In another embodiment, the locking mechanism 150 includes the groove in the surface of the cannula 100, and the dilating element 112 includes the protuberance disposed in the bore hole of the dilating element 112.

Figure 7:
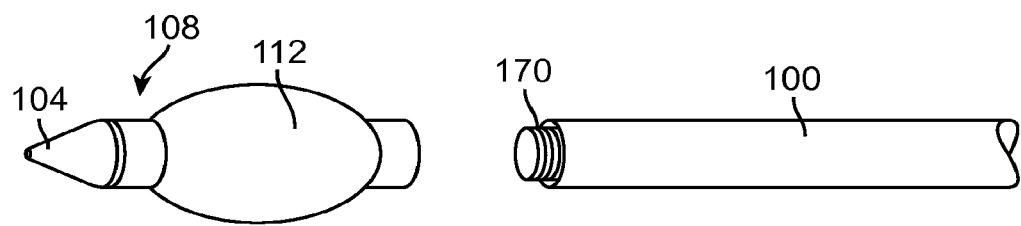
FIG. 7 is an exploded view illustrating the removable module of tip and dilating element on a cannula in accordance with another embodiment of the present invention.

FIG. 7 illustrates an exploded view of an embodiment of cannula 100 in which the tip 104 and the dilating element 112 are fixably coupled together as a unit, and are detachable from the distal end of cannula 100. This embodiment allows convenient change of dilating elements 112 by simply removing the dilating element 112 and tip 104 unit for replacement with an alternate dilating element 112 of different dimension and tip 104 unit. Threads 170 positioned at the distal end of the cannula 100 allows a threaded bore hole 154 (not shown) in the dilating element 112 or tip 104 unit to couple to the threaded shaft 170. This embodiment employing detachable or interchangeable dilating elements 112 allows the surgeon to control the size of the surgical cavity being dissected in tissue. This is accomplished by coupling dilating elements 112 of differing outer dimensions 132 to the cannula 100 which, in turn, enlarge the surgical cavity to sizes corresponding substantially to the dimensions 132 of the dilating elements 112. Different surgical cavities require different amounts of enlargement and therefore the surgeon may select the amount of enlargement provided by the cannula 100 in a specific surgical cavity in accordance with the multiple dilating elements 112 that may be attached and utilized in succession in accordance with the described embodiments of the present invention.

Figure 8:
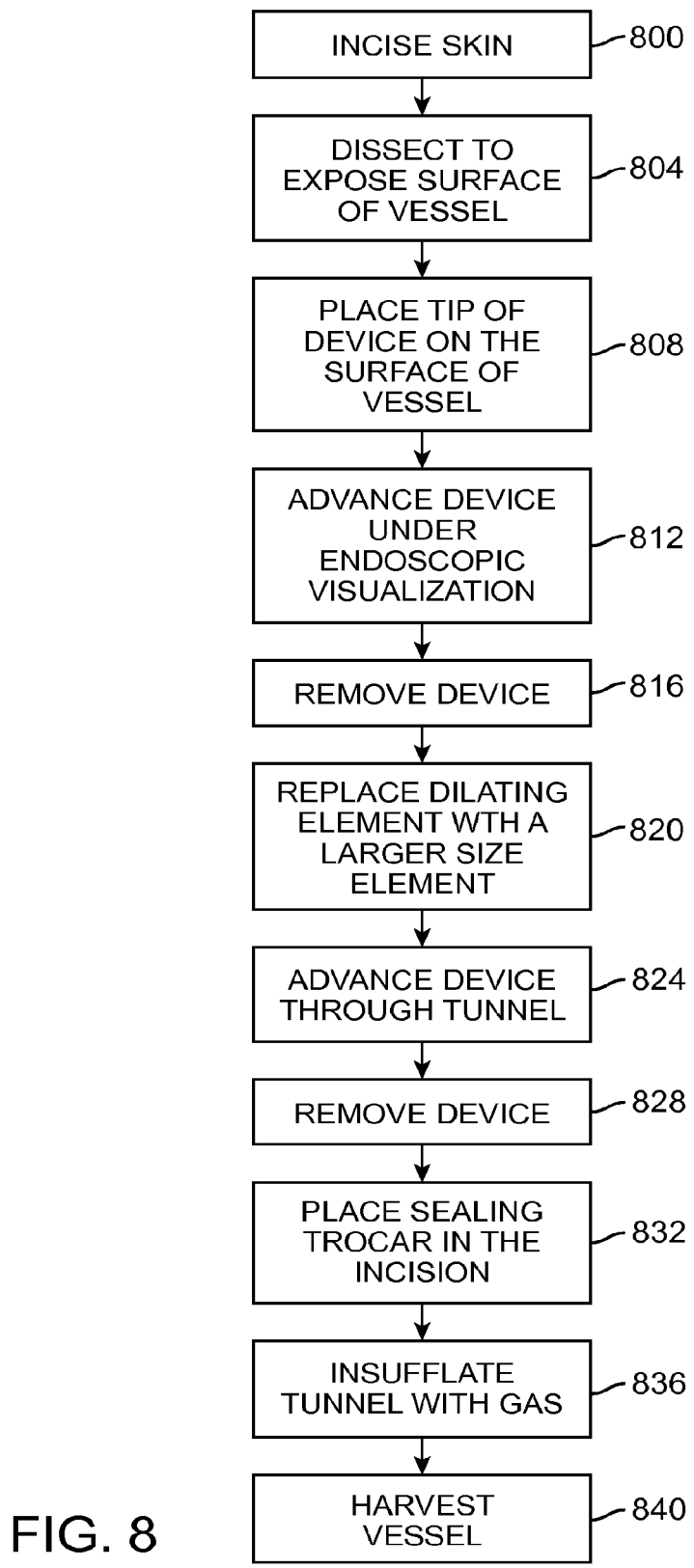
FIG. 8 is a flow chart illustrating the operation of the interchangeable dilating element embodiment of the cannula in accordance with the present invention.

The flow chart of FIG. 8 illustrates a method for isolating a target vessel using the detachable dilating element 112. The surgeon incises 800 the skin and dissects 804 to expose the adventitial surface of the target vessel. The surgeon next places 808 the transparent tapered tip 104 on the adventitial surface of the vessel. The cannula 100 is advanced 812 under endoscopic visualization through the tip 104 until the target vessel is sufficiently isolated. The cannula 100 is removed 816 after establishing a subcutaneous tunnel or surgical cavity adjacent the target vessel which is more constricted than desirable, and therefore requires greater enlargement. The dilating element 112 is then removed and replaced 820 with a larger dilating element 112 and the cannula 100 is again advanced 824 through the tunnel until the surgical cavity is sufficiently dissected using interchangeable dilating elements 112 in a succession of progressively larger dimensions as necessary to attain the required amount of enlargement of the surgical cavity. The cannula 100 is removed 828 and a sealing trocar is placed 832 in the incision and the tunnel is insufflated 836 with gas under pressure to facilitate harvesting the vessel 840.

Figure 9A:
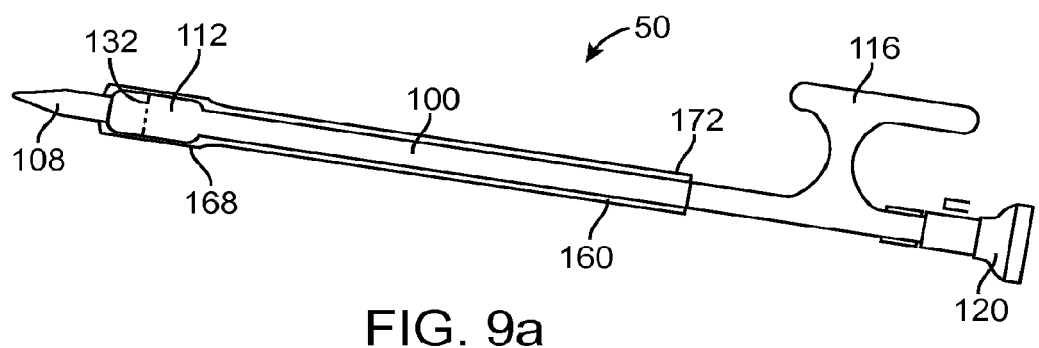
FIG. 9a is a cut-away side sectional view of an embodiment of the present invention including a retractable sheath illustrated in an extended position.
Figure 9B:
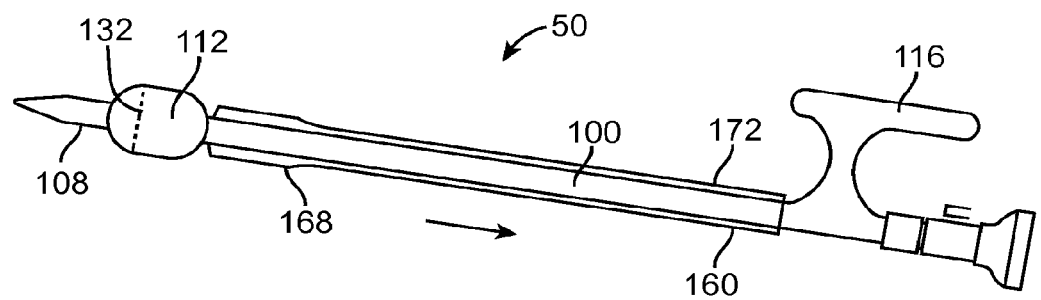
FIG. 9b is a cut-away side sectional view of the embodiment of FIG. 9a with the retractable sheath illustrated in retracted position.

The cut-away side sectional views of FIGS. 9a and 9b illustrate an alternate embodiment of cannula 100 in which a slidable sheath 160 is employed to reduce the outer dimension 132 of the dilating element 112. In this embodiment, the dilating element 112 includes resiliently compressible foam, as described above. The sheath may be formed as a plastic tube which is slidably disposed on the cannula 100 and which has a distal end 168 and a proximal end 172.

Upon sliding or extending the sheath 160 in a distal direction, the distal end 168 of the sheath 160 encases the dilating element 112 and thereby compresses the dilating element 112 to a reduced dimension 132. Upon retracting the sheath 160 by sliding the sheath 160 in a proximal direction, the distal end 168 of the sheath 160 releases the dilating element 112 which resiliently expands to a larger dimension 132, as shown in FIG. 9b. Thus, by compressing the dilating element 112 upon inserting the cannula 100 into an incision, rupture or tearing of the incision is minimized. When properly placed, the sheath 160 is retracted to enable resilient expansion of the dilating element 112, thereby to provide enlargement of the surgical cavity.

Figure 10:
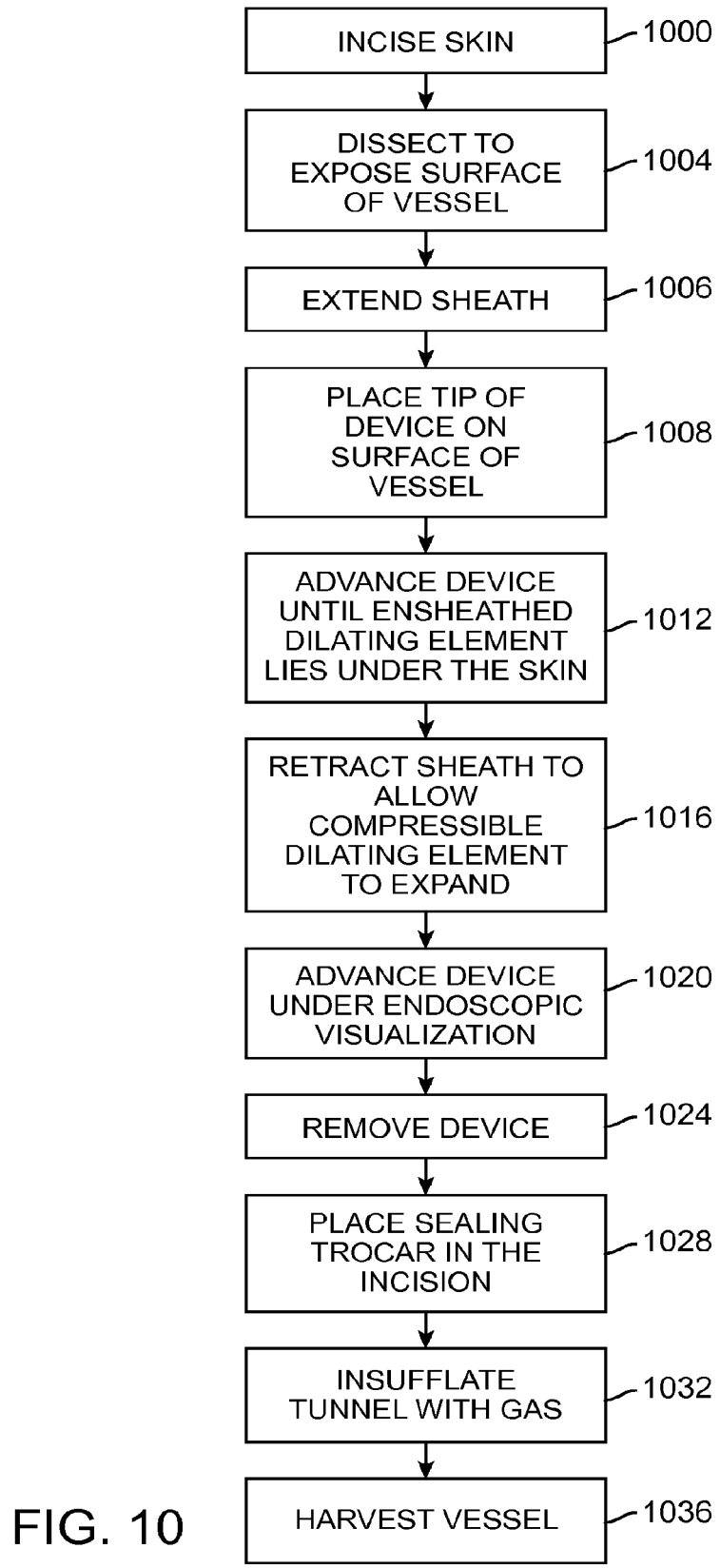
FIG. 10 is a flow chart illustrating the operation of the retractable sheath embodiment of the cannula in accordance with the present invention.

In application, as shown in the flow chart of FIG. 10, the surgeon incises 1000 the skin and dissects 1004 to expose the adventitial surface of the target vessel. The surgeon next extends 1006 the sheath and places 1008 the transparent tapered tip 104 of the cannula 100, with the sheath extended, on the surface of the vessel. The sheath 160 retains the dilating element 112 in compressed configuration as the cannula is advanced 1012 until the ensheathed dilating element 112 is in selected position under the skin. The sheath 160 is retracted 1016 to allow the compressible dilating element 112 to expand. The cannula 100 is advanced 1020 under endoscopic visualization through the tip 104 until the target vessel is sufficiently isolated. The cannula 100 is removed 1024, and a sealing trocar is placed 1028 in the incision and the tunnel is insufflated 1032 with gas under pressure to facilitate harvesting 1036 the isolated vessel.

Therefore the method and apparatus of the present invention facilitate enlargement of a surgical cavity simultaneous with the advancement of the cannula 100 through the surgical cavity, without requiring intermittent manual manipulation of balloons or other similar devices. Additionally, the method and apparatus of the present invention provides for dilating the surgical cavity to different dimensions responsive to interchanging detachable dilating elements 112. Finally, the method and apparatus of the present invention provides for a dilating element 112 which has a compressible resilient dimension for insertion through an incision in a state of compressed dimension for minimizing rupture or tearing of the incision while still providing for enlargement of the surgical cavity in a state of resilient expansion.

The invention claimed is:

1. A tissue dissector system, comprising:
   an elongated shaft having a proximal end and a distal end and a central axis extending therebetween;
   a distal tip having tapered outer walls converging to a blunt end for dissecting tissue, the tip being disposed at the distal end of the shaft to dissect tissue and facilitate passage of the shaft through tissue;
   screw threads positioned on a surface of the shaft for securing the distal tip; and
   a dilating element disposed proximal to the distal tip, the dilating element having a smooth bulbous shaped exterior contour disposed about the central axis to facilitate atraumatic expansion of tissue following dissection by the tapered distal tip advancing through tissue, the dilating element having a cross-sectional dimension of the bulbous shape that is greater than a cross-sectional dimension of the distal end of the shaft and greater than a cross-sectional dimension of the distal tip, wherein a threaded bore hole is formed in the dilating element for engaging the screw threads of the shaft for removably mounting the dilating element to the shaft.

2. The system of claim 1, wherein the dilating element is solid.

3. The system of claim 1, further comprising a spacer disposed between a distal end of the dilating element and a proximal end of the distal tip.

4. The system of claim 3, wherein the spacer has a sufficient length and is positioned between the distal end of the dilating element and a proximal end of the distal tip such that the dilating element is located behind a taper angle of the tapered outer walls of the distal tip.

5. The system of claim 1, wherein the cross-sectional dimension of the bulbous shape of the dilating element is at least two times larger than the cross-section sectional dimension of the distal end of the shaft.

6. The system of claim 5, wherein the cross-sectional dimension of the dilating element is between 15-30 mm.

7. The system of claim 1, wherein the exterior contour of the dilating element has an oval shape.

8. The system of claim 1, wherein the dilating element extends proximally from the distal tip.

9. The system of claim 1, wherein the dilating element is rigid.

10. A tissue dissector system, comprising:
    a cannula system comprising a proximal end and a distal end, wherein the cannula system comprises:
      an elongated body comprising a lumen; and
      an endoscope positionable within the lumen;
    a distal tip having tapered outer walls converging to a blunt end for dissecting tissue, the distal tip being disposed at the distal end of the cannula system to dissect tissue; and
    a solid dilating element of fixed outer dimension removably mounted to a portion of the cannula system located at the distal end and proximal to the distal tip, the dilating element having a smooth bulbous shaped exterior contour to facilitate atraumatic expansion of tissue following dissection by the tapered distal tip, the dilating element having a cross-sectional dimension of the bulbous shape that is greater than a cross-sectional dimension of a distal portion of the elongated body and greater than a cross-sectional dimension of the distal tip,
    wherein the distal tip is removably mounted to the portion of the cannula system and wherein screw threads are positioned on a surface of the portion of the cannula system proximal to the distal tip, and wherein the dilating element further comprises a threaded bore hole for engaging the screw threads and removably mounting the dilating element to the portion of the cannula system.

11. The system of claim 10, further comprising a spacer length disposed between a distal end of each mounted dilating element and a proximal end of the distal tip.

12. The system of claim 10, wherein the cross-sectional dimension of the bulbous shape of each dilating element is at least two times larger than the cross-sectional dimension of the distal end of the elongated body.

13. The system of claim 12, wherein the cross-sectional dimension of the bulbous shape of is between 15-30 mm.

14. The system of claim 10, wherein the exterior contour of at least one of the dilating elements has an oval shape.

15. The system of claim 10, wherein the dilating element extends proximally from the distal tip.

16. A tissue dissector, comprising:
    an elongated shaft having a proximal end and a distal end, wherein the elongated shaft comprises a locking mechanism located at the distal end; and
    dilating unit removably mounted to the shaft distal end, wherein the dilating unit comprises:
      a distal tip having tapered outer walls converging to a blunt end for dissecting tissue, the distal tip being disposed at the distal end of the dilating unit to dissect tissue and facilitate passage of the shaft through tissue; and
      a dilating element having a bulbous shape of cross-sectional dimension greater than a cross-sectional dimension of the distal end of the shaft and greater than a cross-sectional dimension of the distal tip, the dilating element located proximally with respect to the distal tip to facilitate expansion of tissue following dissection by the tapered distal tip passing through tissue, wherein a mating lock adapted to mate with the locking mechanism of the elongated body for mounting the dilating unit to the distal end of the elongated body.

17. The tissue dissector of claim 16, wherein the locking mechanism comprises screw threads positioned on a surface of the shaft, and the mating lock comprises a threaded bore hole formed in the dilating element for engaging the screw threads.

18. The tissue dissector of claim 16, wherein the exterior contour of the dilating element has an oval shape.

19. The tissue dissector of claim 16, wherein the elongate shaft is a cannula.

* * * * *